(12) United States Patent
Xiang et al.

(10) Patent No.: US 8,759,526 B2
(45) Date of Patent: *Jun. 24, 2014

(54) DYES, COMPOSITE DYES, AND OLIGONUCLEOTIDES OR POLYNUCLEOTIDES COMPRISING SUCH DYES—USEFUL OR DETECTION OR QUANTIFICATION OF DESIRABLE TARGET MOLECULES

(75) Inventors: Yuejun Xiang, Bayside, NY (US); Praveen Pande, Holbrook, NY (US); Rajesh Khazanchi, Islandia, NY (US); Elazar Rabbani, New York, NY (US); Dakai Liu, South Setauket, NY (US); Wei Cheng, Jericho, NY (US)

(73) Assignee: Enzo Life Sciences, Inc., Parmingdale, NY (US)

( * ) Notice: Subject to any disclaimer, the term of this patent is extended or adjusted under 35 U.S.C. 154(b) by 1239 days.

This patent is subject to a terminal disclaimer.

(21) Appl. No.: 12/456,515

(22) Filed: Jun. 17, 2009

(65) Prior Publication Data

US 2013/0045480 A1  Feb. 21, 2013

Related U.S. Application Data

(62) Division of application No. 11/137,771, filed on May 24, 2005, now Pat. No. 7,569,695.

(51) Int. Cl.
C07D 215/38 (2006.01)

(52) U.S. Cl.
USPC ........................................... 546/160

(58) Field of Classification Search
USPC ........................................... 546/160
See application file for complete search history.

(56) References Cited

U.S. PATENT DOCUMENTS 8,389,729 B2 *  3/2013  Xiang et al. .................. 546/160

* cited by examiner

Primary Examiner — D M Seaman
(74) Attorney, Agent, or Firm — Anna D. DiGabriele Petti, Esq.

(57) ABSTRACT

The present invention provides dyes, reactive dyes and labeled reagents that may be used in the detection or quantification of desirable target molecules, such as proteins and nucleic acids. Dyes are provided that may be used free in solution where the binding of the dye to the target molecule provides signal generation. Dyes are also provided that comprise reactive groups that may be used to attach the dyes to probes that will bind to desirable target molecules. The novel dyes of the present invention have been modified by the addition of charged and polar groups to provide beneficial properties.

32 Claims, 5 Drawing Sheets

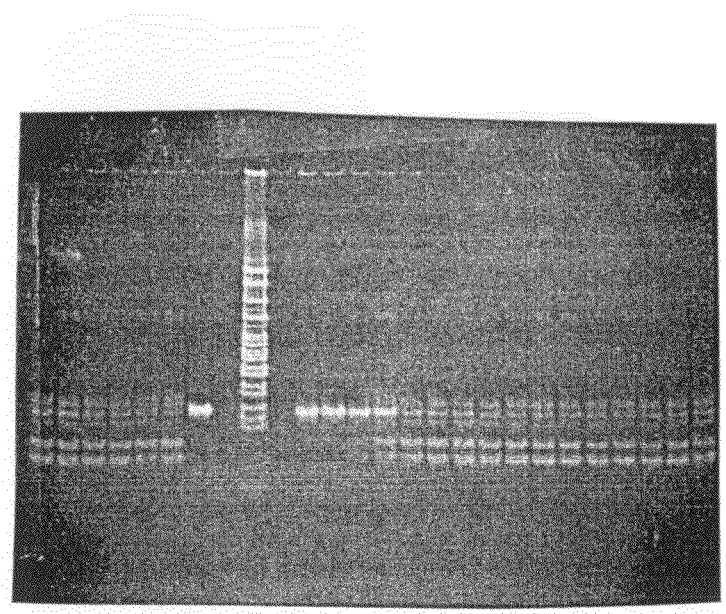

| | | | |
|---|---|---|---|
| 1 | No dye | 14 | 1:100 dilution of Dye 109 |
| 2 | 1:20,000 dilution of SYBR Green | 15 | 1:200 dilution of Dye 109 |
| 3 | 1:4,000 dilution of SYBR Green | 16 | 1:200 dilution of Dye 109 |
| 4 | 1:4,000 dilution of SYBR Green | 17 | 1:400 dilution of Dye 109 |
| 5 | 1:800 dilution of SYBR Green | 18 | 1:400 dilution of Dye 109 |
| 6 | 1:800 dilution of SYBR Green | 19 | 1:800 dilution of Dye 109 |
| 7 | 1:200 dilution of SYBR Green | 20 | 1:800 dilution of Dye 109 |
| 8 | 1:20 dilution of SYBR Green | 21 | 1:1600 dilution of Dye 109 |
| 9 | Msp I digest of pBR322 | 22 | 1:1600 dilution of Dye 109 |
| 10 | Undiluted Dye 109 | 23 | 1:3200 dilution of Dye 109 |
| 11 | 1:25 dilution of Dye 109 | 24 | 1:3200 dilution of Dye 109 |
| 12 | 1:25 dilution of Dye 109 | 25 | 1:6400 dilution of Dye 109 |
| 13 | 1:100 dilution of Dye 109 | 26 | 1:12,800 dilution of Dye 109 |

Figure 1

Amplification samples from Example 34 assayed by gel electrophoresis

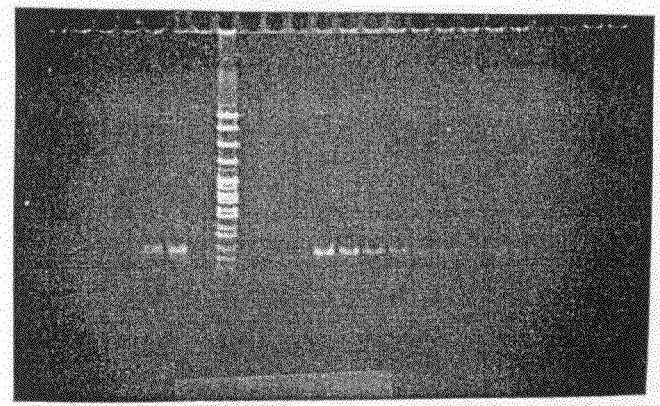

20 Cycles

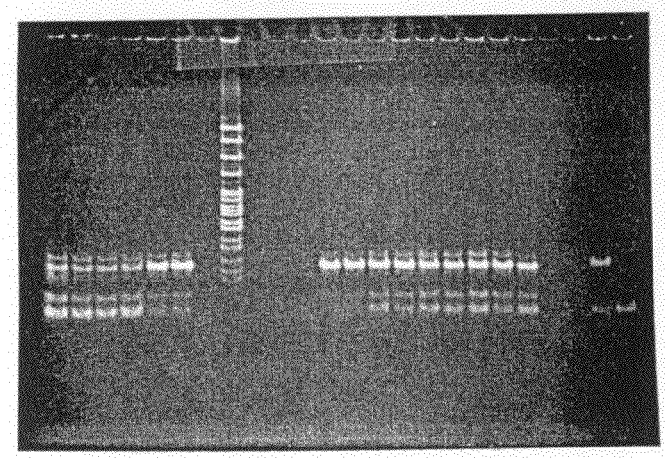

40 Cycles

| | | | |
|---|---|---|---|
| 1 | No dye | 13 | 1:10 dilution of Dye 109 |
| 2 | 1:4,000 dilution of SYBR Green | 14 | 1:15 dilution of Dye 109 |
| 3 | 1:800 dilution of SYBR Green | 15 | 1:15 dilution of Dye 109 |
| 4 | 1:800 dilution of SYBR Green | 16 | 1:20 dilution of Dye 109 |
| 5 | 1:200 dilution of SYBR Green | 17 | 1:20 dilution of Dye 109 |
| 6 | 1:200 dilution of SYBR Green | 18 | 1:25 dilution of Dye 109 |
| 7 | 1:20 dilution of SYBR Green | 19 | 1:25 dilution of Dye 109 |
| 8 | Msp I digest of pBR322 | 20 | 1:200 dilution of Dye 109 |
| 9 | Undiluted Dye 109 | 21 | 1:200 SYBR Green (No target) |
| 10 | 1:5 dilution of Dye 109 | 22 | 1:4000 SYBR Green (No target) |
| 11 | 1:5 dilution of Dye 109 | 23 | 1:10 Dye 109 (No target) |
| 12 | 1:10 dilution of Dye 109 | 24 | 1:25 Dye 109 (No target) |

Figure 2

Amplification samples from Example 35 assayed by gel electrophoresis

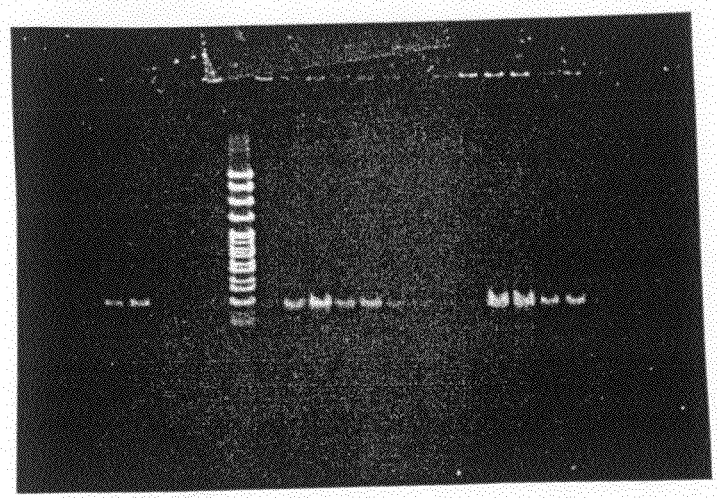

| | | | |
|---|---|---|---|
| 1 | No Dye | 14 | 1:100 dilution of Dye 122 |
| 2 | No Dye | 15 | 1:300 dilution of Dye 122 |
| 3 | 1:4000 dilution of SYBR Green | 16 | 1:1000 dilution of Dye 122 |
| 4 | 1:800 dilution of SYBR Green | 17 | 1:5000 dilution of Dye 122 |
| 5 | 1:800 dilution of SYBR Green | 18 | 1:10 dilution of Dye 109a |
| 6 | 1:200 dilution of SYBR Green | 19 | 1:30 dilution of Dye 109a |
| 7 | 1:200 dilution of SYBR Green | 20 | 1:30 dilution of Dye 109a |
| 8 | 1:20 dilution of SYBR Green | 21 | 1:100 dilution of Dye 109a |
| 9 | Msp I digest of pBR322 | 22 | 1:100 dilution of Dye 109a |
| 10 | 1:10 dilution of Dye 122 | 23 | 1:300 dilution of Dye 109a |
| 11 | 1:30 dilution of Dye 122 | 24 | 1:1000 dilution of Dye 109a |
| 12 | 1:30 dilution of Dye 122 | 25 | 1:800 SYBR Green (No target) |
| 13 | 1:100 dilution of Dye 122 | 26 | 1:30 Dye 109a (No target) |

Figure 3

Amplification samples from Example 36 assayed by gel electrophoresis

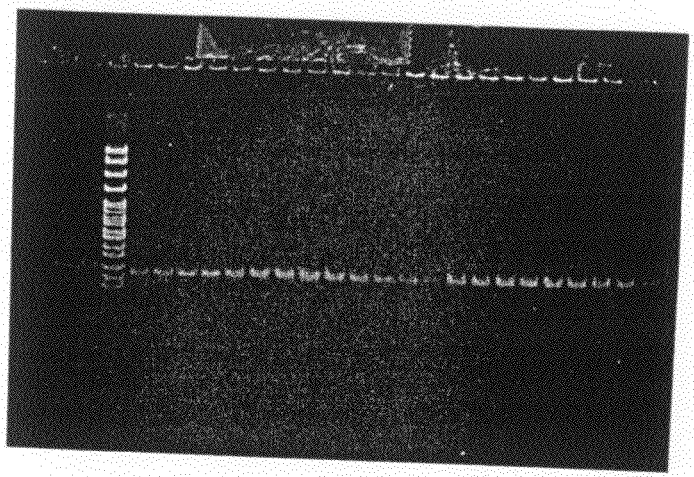

| | | | |
|---|---|---|---|
| 1 | No Dye | 14 | 1:75 dilution of Dye 122 |
| 2 | 1:1000 dilution of SYBR Green | 15 | 1:100 dilution of Dye 122 |
| 3 | 1:500 dilution of SYBR Green | 16 | 1:20 dilution of Dye 109a |
| 4 | Msp I digestion of pBR322 | 17 | 1:20 dilution of Dye 109a |
| 5 | 1:20 dilution of Dye 122 | 18 | 1:25 dilution of Dye 109a |
| 6 | 1:20 dilution of Dye 122 | 19 | 1:25 dilution of Dye 109a |
| 7 | 1:25 dilution of Dye 122 | 20 | 1:30 dilution of Dye 109a |
| 8 | 1:25 dilution of Dye 122 | 21 | 1:30 dilution of Dye 109a |
| 9 | 1:30 dilution of Dye 122 | 22 | 1:40 dilution of Dye 109a |
| 10 | 1:30 dilution of Dye 122 | 23 | 1:40 dilution of Dye 109a |
| 11 | 1:40 dilution of Dye 122 | 24 | 1:50 dilution of Dye 109a |
| 12 | 1:40 dilution of Dye 122 | 25 | 1:75 dilution of Dye 109a |
| 13 | 1:50 dilution of Dye 122 | 26 | 1:100 dilution of Dye 109a |

Figure 4

Amplification samples using various target input levels from Example 37 assayed by gel electrophoresis

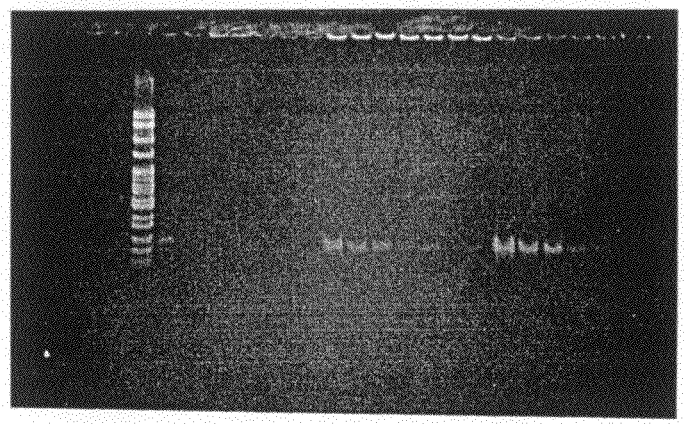

| | | | |
|---|---|---|---|
| 1 | No dye Dilution #2 | 14 | Dye 109a/ Dilution #3 |
| 2 | No Dye Dilution #3 | 15 | Dye 109a/ Dilution #3 |
| 3 | No Dye Dilution #4 | 16 | Dye 109a/ Dilution #4 |
| 4 | No Dye Dilution #5 | 17 | Dye 109a/ Dilution #4 |
| 5 | Msp I digest of pBR322 | 18 | Dye 109a/ Dilution #5 |
| 6 | SYBR Green/ Dilution #2 | 19 | Dye 109a/ Dilution #6 |
| 7 | SYBR Green/ Dilution #3 | 20 | Dye 122/ Dilution #2 |
| 8 | SYBR Green/ Dilution #3 | 21 | Dye 122/ Dilution #3 |
| 9 | SYBR Green/ Dilution #4 | 22 | Dye 122/ Dilution #3 |
| 10 | SYBR Green/ Dilution #4 | 23 | Dye 122/ Dilution #4 |
| 11 | SYBR Green/ Dilution #5 | 24 | Dye 122/ Dilution #4 |
| 12 | SYBR Green/ Dilution #6 | 25 | Dye 122/ Dilution #5 |
| 13 | Dye 109a/ Dilution #2 | 26 | Dye 122/ Dilution #6 |

Figure 5

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catgatccgg atgggaggtg                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcacatccgg atagtgaata ga                                           22

<210> SEQ ID NO 3
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
catgatccgg atgggaggtg ggtctgaaac gataatggtg agtatccctg cctaactcta  60
ttcactatcc ggatgtgc                                                78

DYES, COMPOSITE DYES, AND OLIGONUCLEOTIDES OR POLYNUCLEOTIDES COMPRISING SUCH DYES—USEFUL OR DETECTION OR QUANTIFICATION OF DESIRABLE TARGET MOLECULES

RELATED APPLICATION DATA

This application is a divisional of U.S. patent application Ser. No. 11/137,771, filed on May 24, 2005, now allowed, the contents of which are incorporated herein by reference. This application claims priority to the aforementioned Ser. No. 11/137,771, filed on May 24, 2005.

FIELD OF THE INVENTION

This invention relates to field of labeling compositions, reagents and processes that are useful in applications related to the detection, quantification and localization of target molecules of interest that include nucleic acids and proteins.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

There are a variety of properties that might be desirable for dyes that are intended for use as markers for detection of proteins or nucleic acid hybridization. These can include the ability to bind to a protein, lipid or nucleic acid, the capability of incorporation into nucleic acids by enzymatic means when attached to a nucleotide, a lack of steric hindrance that could potentially interfere with hybridization, water solubility, lack of aggregation, ability to intercalate into double-stranded nucleic acids and the presence of a reactive group that allows attachment of the dye to a nucleotide or other desirable target. Suitable dyes could have many of these properties but do not need to have them all. For instance, the ability to intercalate may allow detection of hybridization events in the presence of unhybridized probes or it may provide increased hybridization stabilization. Examples of these applications are disclosed in European Patent Application EP 0 231 495, U.S. Pat. No. 5,994,056 and U.S. Pat. No. 6,174,670, all of which are incorporated by reference. Similarly, the ability to be incorporated by an enzyme is a useful property when carrying out enzymatic labeling of nucleic acids. Labels that are inhibitory towards incorporation can still be used in some methods where nucleic acids are chemically synthesized rather than using enzymatic means. Also, nucleotides with reactive groups such as allyl-amine may be incorporated enzymatically into nucleic acids and then in a second step they are post-synthetically modified by attachment of dyes. Steric hindrance may be compensated to some degree by the nature of the linker joining the dye to a nucleotide with regard to both the length and the constituents of the linker. For a discussion of this last point, see U.S. Patent Application Ser. No. 2003/0225247, hereby incorporated by reference.

The particular spectral characteristics of dyes are also important qualities. Although broad-spectrum white light can be used as a source of excitation, lasers with defined set wavelengths are most commonly employed. As such, dyes that would find most immediate use would have excitation wavelengths that can make use of such laser emissions. Emission wavelengths are of a more flexible nature since filters can be used to isolate a particular part of the spectrum. However, it should be noted that there are a number of machines used for detection of labeled nucleic acids that have been designed with dyes that are commonly used. For instance, there are a number of slide scanners that have been optimized for detection of nucleic acids labeled with the Cy3 and Cy5 dyes described by Waggoner et al. in U.S. Pat. No. 5,268,486 (incorporated herein by reference). On the other hand, the availability of dyes that have useful properties but have wavelengths that are not commonly used can prove to be an incentive to adopt lasers with compatible wavelengths.

A set of dyes with well separated emission spectra may find use where more than one fluorophor is to be used at the same time. Well known applications in this are immunostaining for various proteins in cells, in situ hybridization for multiple targets, non-radioactive sequencing, nucleic acid array analysis, protein array analysis, as well as non-specific cellular staining with dyes having general affinities for proteins or lipids. On the other hand, overlapping spectral characteristics also have applications; for instance, emission by one fluorophor may be used to excite a second fluorophor through energy transfer when distances are sufficiently close.

Among the dyes that have been most widely used as markers for proteins and nucleic acid labeling are members of the xanthene, coumarin, cyanine and asymmetric cyanine dye families. Xanthene dyes are among the earliest dyes used for biological staining, where fluorescein was used to work out many of the techniques for labeling proteins and nucleic acids. The basic structure of fluorescein molecules can be depicted as:

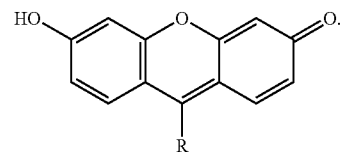

Related xanthene compounds that have also been used as labels include rhodols and rhodamines. Their basic structure is as follows:

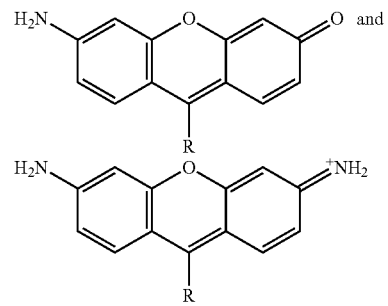

The R group attached to the central structure is typically a substituted phenyl group although as described in U.S. Patent Application Ser. No. 2003/0225247 (hereby incorporated by reference), aphenylic versions are also suitable as dyes.

Another family of dyes that have enjoyed widespread use is based upon derivatives of coumarin. The basic structure of coumarin is as follows:

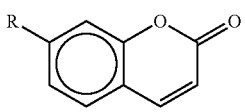

Typically, coumarin derivatives will be dyes when R is an OH or an amine group. Useful compounds have also been made where R is further modified such that an enzymatic cleavage event converts the R group into an OH or amine group. Thus this proto-dye or dye precursor can be used as marker for the presence of an enzyme that is capable of converting a coumarin compound into a fluorescent dye. Discussions of such methods are disclosed in U.S. Pat. No. 5,696,157 and U.S. Pat. No. 5,830,912, both of which are incorporated by reference.

As described above, a large number of useful dyes are based upon cyanine dyes. The basic structure of Cyanine dyes is as follows

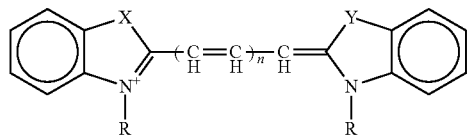

As will be discussed later, major factors in the particular spectral qualities of these dyes is dependent upon the number "n", the nature of "X" and "Y" and functional groups that extend the aromaticity of the dyes.

Other compounds that were functionally considered to be Cyanine-type dyes (see U.S. Pat. No. 5,268,486 hereby incorporated by reference) are the merocyanine and styryl dyes whose structures are:

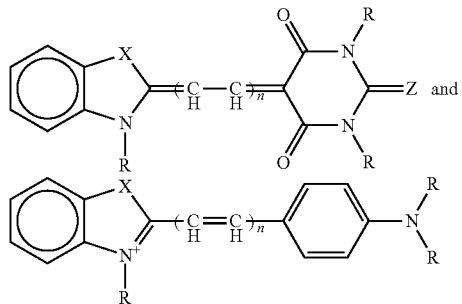

There are a variety of atoms that have been used in the X and Y positions. These have included carbon, sulfur, oxygen, nitrogen and selenium. When X or Y is a carbon, this portion of the dye is an indolinium moiety. When X or Y is substituted by sulfur, oxygen or nitrogen this portion is respectively described as a benzothiazolium, benzoxazolium or a benzimidazolium moiety.

Another version of styryl dyes can have picoline or quinoline moieties instead of the benzazolium group, thereby having the structures:

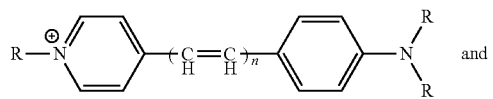 and

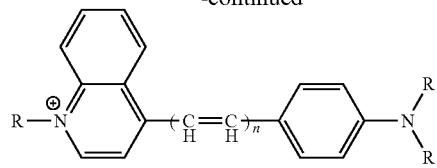

Asymmetric cyanine dyes contain one portion that is essentially the benzazolium portion of the cyanine dye family but connected to this portion by the methine bridge is a different aromatic compound. Their structure is as follows:

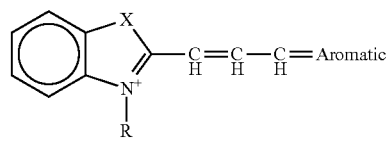

The aromatic moiety can be a six membered aromatic or heteroaromatic ring

Improvements to these dyes have been carried out by substitution of various groups onto the basic structure, i.e. on the carbons and nitrogens of the preceding structures or where H or R groups are featured. Additionally, other rings may be fused to various parts of the rings in the structures above, thereby generating more complex structures. These modifications have led to shifts in the excitation and emission characteristics of the dyes that allow a large number of dyes with same basic structure but having different spectral characteristics, i.e. modifications can be made in their structure that can alter the particular wavelengths where these compounds will absorb and fluoresce light. As described above, the cyanine dyes can have a general structure comprising two benzazolium-based rings connected by a series of conjugated double bonds. The dyes are classified by the number (n) of central double bonds connecting the two ring structures; monocarbocyanine or trimethinecarbocyanine when n=1; dicarbocyanine or pentamethinecarbocyanine when n=2; and tricarbocyanine or heptamethinecarbocyanine when n=3. The spectral characteristics of the cyanine dyes have been observed to follow specific empirical rules. For example, each additional conjugated double bond between the rings usually raise the absorption and emission maximum about 100 nm. Thus, when a compound with n=1 has a maximum absorption of approximately 550 nm, equivalent compounds with n=2 and n=3 can have maximum absorptions of 650 nm and 750 nm respectively. Addition of aromatic groups to the sides of the molecules has lesser effects and may shift the absorption by 15 nm to a longer wavelength. The groups comprising the indolenine ring can also contribute to the absorption and emission characteristics. Using the values obtained with gem-dimethyl group as a reference point, oxygen substituted in the ring for the gem-dimethyl group can decrease the absorption and emission maxima by approximately 50 nm. In contrast, substitution of sulfur can increase the absorption and emission maxima by about 25 nm. R groups on the aromatic rings such as alkyl, alkyl-sulfonate and alkyl-carboxylate usually have little effect on the absorption and emission maxima of the cyanine dyes (U.S. Pat. No. 6,110,630, hereby incorporated by reference).

As described above, alteration of spectral qualities is only one useful modification that can be made to a dye. In another instance, modification of a dye by a sulfonate group may increase the stability of many dyes and thereby resist "bleaching" after illumination. Modification of dyes by sulfonation was later applied in the modification of cyanine dyes with reactive groups (U.S. Pat. No. 5,569,766 hereby incorporated by reference), where it was reported that the sulfonation decreases aggregation of labeled materials. It was further applied to xanthenes, coumarins and the non-benzazolium portion of asymmetric cyanine dyes (U.S. Pat. No. 5,436,134, U.S. Pat. No. 6,130,101 and U.S. Pat. No. 5,696,157, all of which are hereby incorporated by reference). Modifications of dyes have also been made to increase their affinity or selectivity towards binding to nucleic acids (European Patent Application Serial No. EPO 231495, U.S. Patent Application Serial No. 2003/0225247 and U.S. Pat. No. 5,658,751, all of which are incorporated by reference).

In many cases, the utility of these dyes has been achieved by synthesis of compounds with a reactive group that allows attachment of the dye to a target molecule. For instance, although cyanine dyes in themselves had been known for many years, it was only when derivatives were described with reactive groups (U.S. Pat. No. 5,268,486 hereby incorporated by reference) that they found widespread use in labeling proteins and nucleic acids. Their versatility was then increased by disclosure of other groups that could be used to attach cyanine dyes to suitable partners (U.S. Pat. No. 6,114,350 and U.S. Patent Application Ser. No. 2003/0225247, both of which are hereby incorporated by reference). An exemplary list of electrophilic groups and corresponding nucleophilic groups that can be used for these purposes are given in Table 1 of U.S. Pat. No. 6,348,596 (hereby incorporated by reference).

A variety of linker arms may be used to attach dyes to targets. Commonly used constituents for linkers are chains that contain varying amounts of carbon, nitrogen, oxygen and sulfur. Examples of linkers using some of these combinations are given in U.S. Pat. No. 4,707,440, hereby incorporated by reference. Bonds joining together the constituents can be simple carbon-carbon bonds or they may be acyl bonds (U.S. Pat. No. 5,047,519), sulfonamide moieties (U.S. Pat. No. 6,448,008) and polar groups (U.S. Patent Application Ser. No. 2003/0225247) all of which are hereby incorporated by reference.

SUMMARY OF THE INVENTION

The present invention provides a dye having the formula:

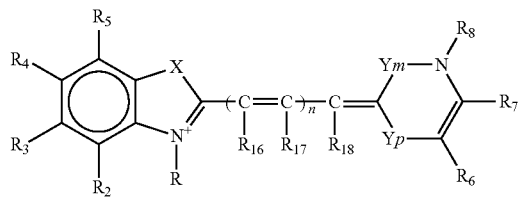

wherein X comprises $CR^{11}R^{12}$, $NR^{11}$, O, S or Se where $R^{11}$ and $R^{12}$ independently comprise hydrogen, a halogen, an amino group, or an alkyl group. The alkyl group is saturated or unsaturated, linear or branched, substituted or unsubstituted, an alkoxy group wherein the alkoxy group is saturated or unsaturated, branched or linear, substituted or unsubstituted, or when taken together, $R^{11}$ and $R^{12}$ form a five- or six-membered ring. In the formula given above, n can be 0, 1, 2 or 3; wherein Y is $—CR^9=CR^{10}$. In the formula, m and p can have values of 0 or 1 and m+p=1; wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2). Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$) its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S. Q(1) is attached directly, or indirectly through a linker arm comprising carbon, sulfur, oxygen, nitrogen, or any combinations thereof, wherein the linker arm may be saturated or unsaturated, linear or branched, substituted or unsubstituted, or any combinations thereof and wherein when Q(1) is a sulfonamide, it does not comprise a terminal reactive group or a linker joining the dye to a target molecule. Q(2) comprises a sulfoxide ($SOR^{13}$), a sulfone ($SO_2CR^{13}R^{14}R^{15}$), a sulfonamide ($SO_2NR^{13}R^{14}$), a phosphonate ($PO_3^=$), a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}R^{15}NR^{19}R^{20}$) a phosphoramidite ($PO_2R^{19}NR^{13}R^{14}$) or its thioanalogue ($POSR^{19}NR^{13}R^{14}$), wherein any of E can independently comprise O or S. In this dye, Q(2) is attached directly, or indirectly through a linker arm comprising carbon, sulfur, oxygen, nitrogen, or any combinations thereof, where the linker arm may be saturated or unsaturated, linear or branched, substituted or unsubstituted or any combinations thereof. In this dye, when Q(2) is a sulfonamide, it does not comprise a terminal reactive group or a linker joining the dye to a target molecule. In this dye, $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein the alkoxy group is saturated or unsaturated, branched or linear, substituted or unsubstituted, or when taken together $R^{13}$ and $R^{14}$ form a five- or six-membered ring. In this dye, $R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, an alkyl group wherein the alkyl group is saturated or unsaturated, linear or branched, substituted or unsubstituted, an alkoxy group that is saturated or unsaturated, branched or linear, substituted or unsubstituted, or when taken together, $R^2$ and $R^3$, $R^3$ and $R^4$, $R^4$ and $R^5$, $R^6$ and $R^7$, and $R^7$ and $R^8$ may form a five- or six-membered ring; or when taken together $R^1$ and $R^{16}$, $R^{11}$ and $R^{16}$, $R^{16}$ and $R^{17}$, $R^{17}$ and $R^{18}$, and $R^{18}$ and $R^9$ may form a five- or six-membered ring. In this dye Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{19}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$). In the foregoing, E can be independently O or S; wherein Z is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof. Any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain wherein the side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein the alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five- or six-membered ring, and wherein any of $R^{25}$, $R^{26}$ or $R^{27}$ may further comprise the heteroatom containing side chain.

The present invention also provides a dye having the formula:

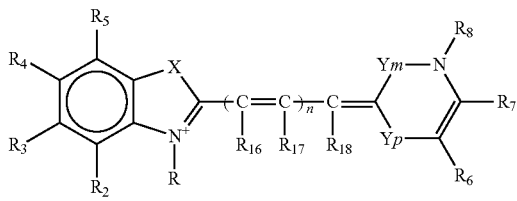

wherein X comprises $CR^{11}R^{12}$, $NR^{11}$, O, S or Se where $R^{11}$ and $R^{12}$ independently comprise hydrogen, a halogen, an amino group, or an alkyl group. The alkyl group is saturated or unsaturated, linear or branched, substituted or unsubstituted, an alkoxy group wherein the alkoxy group is saturated or unsaturated, branched or linear, substituted or unsubstituted, or when taken together, $R^{11}$ and $R^{12}$ form a five- or six-membered ring. In the formula above, n can be 0, 1, 2 or 3; Y is —$CR^9$=$CR^{10}$—; m and p can have values of 0 or 1 and m+p=1; and wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2). Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$) a phosphoramidite ($PO_2R^{19}NR^{13}R^{14}$) or its thioanalogue ($POSR^{19}NR^{13}R^{14}$) wherein any of E can independently comprise O or S. In this dye, Q(1) is attached directly, or indirectly through a linker arm comprising carbon, sulfur, oxygen, nitrogen, or any combinations thereof, wherein the linker arm may be saturated or unsaturated, linear or branched, substituted or unsubstituted, or any combinations thereof and wherein when Q(1) is a sulfonamide, it does not comprise a terminal reactive group or a linker joining the dye to a target molecule. In the dye of the present invention Q(2) comprises a sulfoxide ($SOR^{13}$), a sulfone ($SO_2CR^{13}R^{14}R^{15}$), a sulfonamide ($SO_2NR^{13}R^{14}$), a phosphonate ($PO_3^=$), a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{74}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S. In this dye Q(2) is attached directly, or indirectly through a linker arm comprising carbon, sulfur, oxygen, nitrogen, or any combinations thereof, wherein the linker arm may be saturated or unsaturated, linear or branched, substituted or unsubstituted or any combinations thereof and wherein when Q(2) is a sulfonamide, it does not comprise a terminal reactive group or a linker joining the dye to a target molecule. In the foregoing formulae, $R^{13}$, $R^{14}$, $R^{15}$, $R^{19}$ and $R^{20}$ can be hydrogen, a halogen, an amino group or an alkyl group. The alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five- or six-membered ring. In this dye, $R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, or an alkyl group wherein the alkyl group is saturated or unsaturated, linear or branched, substituted or unsubstituted, an alkoxy group that is saturated or unsaturated, branched or linear, substituted or unsubstituted, or when taken together, $R^2$ and $R^3$, $R^3$ and $R^4$, $R^4$ and $R^5$, $R^6$ and $R^7$, and $R^7$ and $R^8$ may form a five- or six-membered ring; or when taken together $R^1$ and $R^{16}$, $R^{11}$ and $R^{16}$, $R^{16}$ and $R^{17}$, $R^{17}$ and $R^{18}$, and $R^{18}$ and $R^9$ may form a five- or six-membered ring. In the dye Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S and the structures are as described previously. As just provided Z is attached directly, or indirectly through a linker arm comprising carbon, sulfur, oxygen, nitrogen, or any combinations thereof, wherein the linker arm may be saturated or unsaturated, linear or branched, substituted or unsubstituted or any combinations thereof.

Any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain, wherein the side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein the alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five- or six-membered ring, and wherein any of $R^{25}$, $R^{26}$ or $R^{27}$ may further comprise the heteroatom containing side chain. In this dye, at least one of $R^1$, $R^2$, $R^3$, $R^4$, $R^5$, $R^6$, $R^7$, $R^8$, $R^9$, $R^{10}$, $R^{13}$, $R^{14}$, or $R^{15}$ further comprises a nucleophilic reactive group, an electrophilic reactive group, a terminal alkene, a terminal alkyne, a coordinate group or an alkylating agent.

Also provided by the present invention is a composition comprising a first portion and a second portion, wherein the first portion comprises a dye and the second portion comprises a target molecule, the dye having the formula:

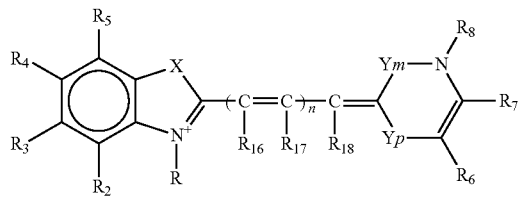

wherein X comprises $CR^{11}R^{12}$, $NR^{11}$, O, S or Se where $R^{11}$ and $R^{12}$ independently comprise hydrogen, a halogen, an amino group, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together, $R^{11}$ and $R^{12}$ form a five- or six-membered ring. In this composition and the formula above, n can be 0, 1, 2 or 3; Y is —$CR^9$=$CR^{10}$—; m and p can have values of 0 or 1 and m+p=1; and wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2). In this composition Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{15}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S. In this composition Q(1) is attached directly, or indirectly through a linker arm comprising carbon, sulfur, oxygen, nitrogen, or any combinations thereof and wherein the linker arm may be saturated or unsaturated, linear or branched, substituted or unsubstituted, or any combinations thereof and wherein when Q(1) is a sulfonamide, it does not comprise a terminal reactive group or a linker joining the dye to a target molecule. Q(2) comprises a sulfoxide ($SOR^{13}$), a sulfone ($SO_2CR^{13}R^{14}R^{15}$), a sulfonamide ($SO_2NR^{13}R^{14}$), a phosphonate ($PO_3^=$), a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S. In this composition Q(2) is attached directly, or indirectly through a linker arm comprising carbon, sulfur, oxygen, nitrogen, or any combinations thereof and wherein the linker arm may be saturated or unsaturated, linear or branched, substituted or unsubstituted, or any combinations thereof and wherein when Q(2) is a sulfonamide, it does not comprise a terminal reactive group or a linker joining the dye to a target molecule. In the foregoing formulae $R^{13}$, $R^{14}$, $R^{15}$, $R^{19}$ and $R^{20}$ can be hydrogen, a halogen, an amino group, an alkyl group wherein the alkyl group is saturated or unsaturated, linear or branched, substituted or unsubstituted, an alkoxy group wherein the alkoxy group is saturated or unsaturated, branched or linear, substituted or unsubstituted, or when taken together $R^{13}$ and $R^{14}$ form a five- or six-membered ring. $R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, an alkyl group wherein the alkyl group is saturated or unsaturated, linear or branched, substituted or unsubstituted, an alkoxy group that is saturated or unsaturated, branched or linear, substituted or unsubstituted, or when taken together, $R^2$ and $R^3$, $R^3$ and $R^4$, $R^4$ and $R^5$, $R^6$ and $R^7$, and $R^7$ and $R^8$ may form a five- or six-membered ring; or when taken together $R^1$ and $R^{16}$, $R^{11}$ and $R^{16}$, $R^{16}$ and $R^{17}$, $R^{17}$ and $R^{18}$, and $R^{18}$ and $R^9$ may form a five- or six-membered ring. In this composition Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$) a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S and the structures are as described previously. In this composition Z is attached directly, or indirectly through a linker arm comprising carbon, sulfur, oxygen, nitrogen, or any combinations thereof and wherein the linker arm may be saturated or unsaturated, linear or branched, substituted or unsubstituted or any combinations thereof. In this composition.

Any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain wherein the side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein the alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five- or six-membered ring, and wherein any of $R^{25}$, $R^{26}$ or $R^{27}$ may further comprise the heteroatom containing side. At least one of $R^1$, $R^2$, $R^3$, $R^4$, $R^5$, $R^6$, $R^7$, $R^8$, $R^9$, $R^{10}$, $R^{13}$, $R^{14}$, or $R^{15}$ is linked to said second portion.

The present invention further provides a method for detecting the presence or quantity of a target comprising the steps of: a) providing i) a sample where the presence or quantity of a target is desired to be detected ii) a composition comprising a first portion and a second portion wherein the first portion comprises a dye and the second portion comprises a target specific moiety, the dye having the formula

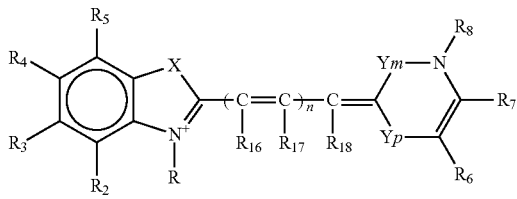

as described and defined above; b) allowing any targets present in the sample i) to bind with the target specific moiety comprising the composition ii); and c) quantifying the amount of the composition ii) bound to any of the target in the sample, thereby detecting the presence or quantity of the target.

Also provided by the invention herein is a method for detecting the presence, location or quantity of a target comprising the steps of: a) providing i) a sample where the presence, location or quantity of a target is desired to be detected, ii) a dye, having the formula:

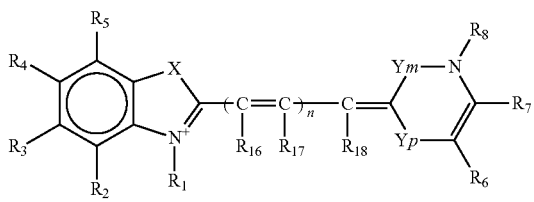

as described and defined above; b) allowing any targets present in the sample i) to bind with the dye ii); and c) detecting the dye ii) bound to any of the target in the sample i), thereby detecting the presence, location or quantity of the target.

Other processes are provided by the present invention including a process for increasing the amount of amplification of a target sequence, the process comprising amplifying the target sequence in the presence of an intercalating compound at a concentration where the efficiency of amplification is increased compared to the efficiency of amplification in the absence of the intercalating compound.

Another process provided by the present invention is for increasing the specificity of amplification of a target sequence, the process comprising amplifying the target sequence in the presence of an intercalating compound at a concentration where the specificity of amplification is increased compared to the specificity of amplification in the absence of the intercalating compound.

Another process of the present invention is for increasing the amount of amplification of a target sequence and for increasing the specificity of amplification of a target sequence, the process comprising amplifying the target sequence in the presence of an intercalating compound at a concentration where (i) the efficiency of amplification is increased compared to the efficiency of the intercalating compound, and (ii) the specificity of amplification is increased compared to the specificity of amplification in the absence of the intercalating compound.

Yet another process by the invention herein is for decreasing the amount of non-target amplification during a target amplification reaction, the process comprising amplifying the target sequence in the presence of an intercalating compound at a concentration where the efficiency of amplification of a non-target sequence is decreased compared to the efficiency of amplification of a non-target sequence in the absence of the intercalating compound.

DESCRIPTION OF THE FIGURES

FIG. 1 is a photograph of samples from Example 33 assayed by gel electrophoresis.
FIG. 2 is a photograph of samples from Example 34 assayed by gel electrophoresis.
FIG. 3 is a photograph of samples from Example 35 assayed by gel electrophoresis.
FIG. 4 is a photograph of samples from Example 36 assayed by gel electrophoresis.
FIG. 5 is a photograph of samples from Example 37 assayed by gel electrophoresis.

DESCRIPTION OF THE INVENTION

The present invention provides dyes, reactive dyes and labeled reagents that may be used in the detection or quantification of desirable target molecules. Some of these dyes may be used free in solution where the binding of the dye to the target molecule provides increase fluorescence. Other dyes of the present invention comprise reactive groups that may be used to attach the dyes to desirable target molecules. The novel dyes of the present invention have been modified by the addition of charged groups as exemplified by sulfonates, phosphates, phosphonates and their derivatives. Other dyes have been modified by the addition of polar groups such as sulfoxide, sulfone and sulfonamide moieties. Dyes may also be modified by both charged and polar groups.

In the present invention, sulfonates are considered to be any group with the formula $SO_3^-$ including both sulfonic acid as well as various sulfonate salts. The addition of a sulfonate group provides a charged moiety that can increase solubility, inhibit bleaching and reduce aggregation. The addition of phosphonate ($PO_3^=$), phosphate (O—$PO_3^=$) moieties or their derivatives may also provide such qualities. Transformation of the foregoing charged species into esters may convert a charged group into a polar group. Derivatives that may find use with the present invention can include thioanalogues such as thiophosphates, thiophosphonates and thioesters. Other derivatives that may find use can include phosphoramides and phosphonamides.

In the present invention, sulfones are considered to be any groups that have the formula C—$SO_2$—C where carbon atoms are attached to the intervening sulfur atom. One of the carbon atoms may be part of a ring structure of the dye or it may part of an intervening alkyl group connecting the sulfone to the dye. When one of the carbons of a sulfone is replaced by a nitrogen atom the group is a sulfonamide.

The presence of the polar groups may help nucleotide incorporation since dyes with polar groups will be less negatively charged than their ionized equivalents and thus be less repelled by the negatively charged phosphate backbone of a nucleic acid template. The sulfone or sulfonamide group can be modified as desired by linkage to other moieties to add desirable properties. It is also understood that the degree of charge or polarity can be determined by the user by the addition of appropriate combinations of charged and polar groups to a dye.

In the present invention, Sulfoxides (SOR$^{13}$), Sulfones (SO$_2$CR$^{13}$R$^{14}$R$^{15}$) and sulfonamides sulfonamides (SO$_2$NR$^{13}$R$^{14}$) are respectively defined as having the structures:

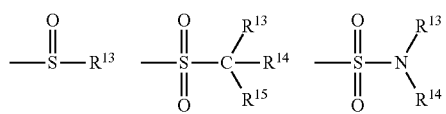

In the present invention, phosphates (PO$_4$≡), their monoesters (PO$_3$⁻ER$^{13}$), diesters (PO$_2$ER$^{13}$ER$^{14}$), are respectively defined as having the structures:

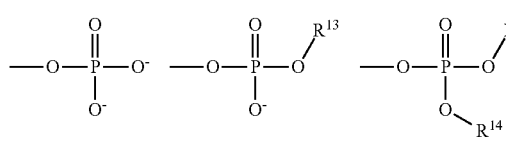

when E is an oxygen in the monoester and diester and

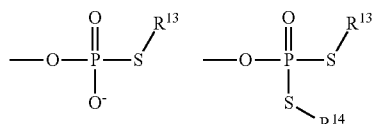

when E is a sulfur.

In the present invention, phosphonates (PO$_3$≡), their esters (PO$_2$⁻ER$^{13}$) and POER$^{13}$ER$^{14}$) are respectively defined as having the structures:

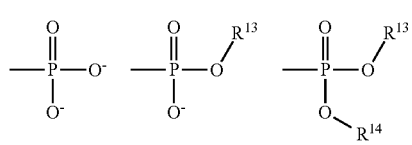

when E is an oxygen in the monoester and diester and

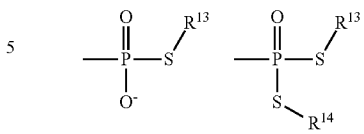

when E is a sulfur.

In the present invention, thiophosphates (PSO$_3$≡), their esters (PSO$_2$⁻ER$^{13}$) and PSOER$^{13}$ER$^{14}$) are respectively defined as having the structures:

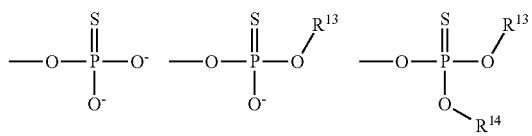

when E is an oxygen in the monoester and diester and

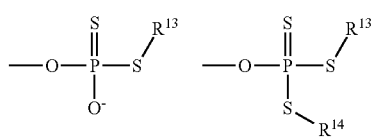

when E is a sulfur.

In the present invention, thiophosphonates (PSO$_2$≡), their esters (PSO⁻ER$^{13}$) and PSER$^{13}$ER$^{14}$) are respectively defined as having the structures:

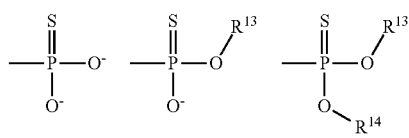

when E is an oxygen in the monoester and diester and

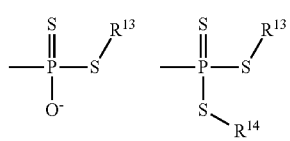

when E is a sulfur

In the present invention, sulfonates (SO$_3$⁻), their esters (SO$_2$ER$^{13}$) are respectively defined as having the structures:

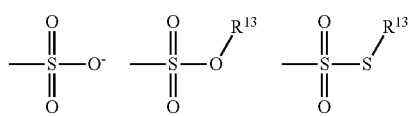

when E is an oxygen or sulfur in the ester linkage.

In the present invention, phosphonamides (PONR$^{13}$R$^{14}$NR$^{19}$R$^{20}$), phosphoramides (PONR$^{13}$R$^{14}$NR$^{15}$NR$^{19}$R$^{20}$) and phosphoramidites (PO$_2$R$^{19}$NR$^{13}$R$^{14}$) are respectively defined as having the structures:

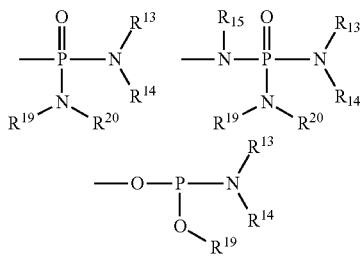

and their thioanalogues (PSNR$^{13}$R$^{14}$NR$^{19}$R$^{20}$), (PSNR$^{13}$R$^{14}$NR$^{19}$NR$^{19}$R$^{20}$) and (POSR$^{19}$NR$^{13}$R$^{14}$) having respectively the structures:

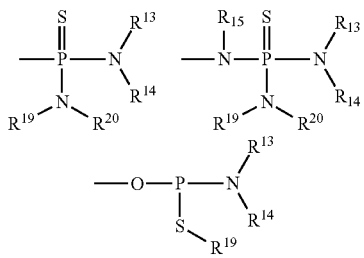

It is also understood that when a dye comprises anionic group, there will also be a cationic counterion present. Any cation may serve this purpose as long as it doesn't interfere with the use of the dye. Examples of cations that may serve as counterions can include but not be limited to hydrogen, sodium, potassium, lithium, calcium, cesium, ammonium, alkyl ammonium, alkoxy ammonium and pyridinium. It is also understood that when a dye comprises a cationic group, there will also be an anionic counterion present. Any anion may serve this purpose as long as it doesn't interfere with the use of the dye. Examples of anions that may serve as counterions can include but not be limited to halides such as a bromide, chloride, fluoride and iodide. Other examples can include but not be limited to perchlorate (ClO$_4^-$), sulfate (SO$_4^=$), sulfonate, alkane sulfonate, aryl sulfonate, phosphate, tosylate, mesylate and tetrafluoroborate moieties. In some cases the counterion or counterions are provided by the dye being a salt where they exist as separate ionic species. In other cases, the counterion or counterions may be present as part of the compound (sometimes called inner salts). It is understood that there may also be a combination of ions that are provided by the compound and salts. With regard to acid moieties that are shown in forms such as COOH it is also understood that these compounds may be found in ionized forms such as COO$^-$.

Alkyl or alkoxy R groups may be substituted or unsubstituted. Examples of substitutions can include but not be limited to one or more fluorine, chlorine, bromine, iodine, hydroxy, carboxy, carbonyl, amino, cyano, nitro or azido groups as well as other alkyl or alkoxy groups. The length of the alkoxy groups may be as desired. For instance, they may independently comprise from 1 to 18 carbons in length. They may be shorter as well, for instance they may be only 1 to 6 carbons in length in a dye molecule of the present invention.

The polar groups, charged groups and other substituents may be connected to the dye directly or they may be connected by a linker arm comprising carbon, nitrogen, sulfur, oxygen or any combination thereof. The linker arm may be saturated or unsaturated, linear or branched, substituted or unsubstituted as well as any combination of the foregoing.

In one aspect of the present invention, novel dyes that are based upon cyanine dyes are disclosed. In one embodiment the dyes have the structure:

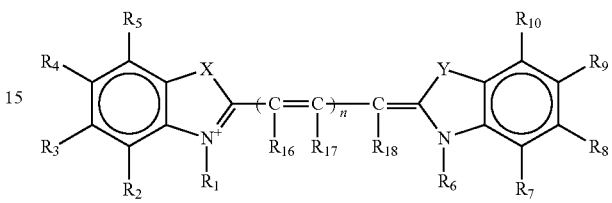

wherein X and Y independently comprise CR$^{11}$R$^{12}$, NR$^{11}$, O, S or Se, wherein R$^{11}$ and R$^{12}$ independently comprise hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, R$^{11}$ and R$^{12}$ comprise a 5 or 6 membered ring;

wherein n can be 0, 1, 2 or 3 wherein at least one of R$^1$, R$^2$, R$^3$, R$^4$, R$^5$, R$^6$, R$^7$, R$^8$, R$^9$, R$^{10}$, R$^{11}$, or R$^{12}$ comprises Q, wherein Q comprises a sulfoxide (SOR$^{13}$), a sulfone (SO$_2$CR$^{13}$R$^{14}$R$^{15}$), a sulfonamide (SO$_2$NR$^{13}$R$^{14}$), a phosphate monoester (PO$_3^-$ER$^{13}$), a phosphate diester (PO$_2$ER$^{13}$ER$^{14}$), a phosphonate monoester (PO$_2^-$ER$^{13}$), a phosphonate diester (POER$^{13}$ER$^{14}$), a thiophosphate (PSO$_3^=$), a thiophosphate monoester (PSO$_2^-$ER$^{13}$), a thiophosphate diester (PSOER$^{13}$ER$^{14}$), a thiophosphonate (PSO$_2^=$), a thiophosphonate monoester (PSO$^-$ER$^{13}$), a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$), or its thioanalogue (POSR$^{19}$NR$^{13}$R$^{14}$), wherein any of E independently comprises O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, Q does not have a terminal reactive group or a linker arm joining the dye to a target molecule;

wherein R$^{13}$, R$^{14}$, R$^{15}$, R$^{16}$, R$^{17}$, R$^{18}$, R$^{19}$, R$^{20}$ and the remaining R$^1$, R$^2$, R$^3$, R$^4$, R$^5$, R$^6$, R$^7$, R$^8$, R$^9$, R$^{10}$, R$^{11}$, and R$^{12}$, independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together R$^2$ and R$^3$, R$^3$ and R$^4$, R$^4$ and R$^5$, R$^7$ and R$^8$, R$^8$ and R$^9$, R$^9$ and R$^{10}$, R$^1$ and R$^{16}$, R$^6$ and R$^{18}$, R$^{11}$ and R$^{16}$, R$^{16}$ and R$^{17}$, R$^{18}$ and R$^{11}$, R$^{13}$ and R$^{14}$, R$^{14}$ and R$^{15}$, R$^{19}$ and R$^{20}$ independently comprise a five or six membered ring;

wherein R$^{13}$, R$^{14}$, R$^{15}$, R$^{16}$, R$^{17}$, R$^{18}$, R$^{19}$, R$^{20}$ and the remaining R$^1$, R$^2$, R$^3$, R$^4$, R$^5$, R$^6$, R$^7$, R$^8$, R$^9$, R$^{10}$, R$^{11}$, and $R^{12}$, independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^2$ and $R^3$, $R^3$ and $R^4$, $R^4$ and $R^5$, $R^7$ and $R^8$, $R^8$ and $R^9$, $R^9$ and $R^{10}$, $R^1$ and $R^{16}$, $R^6$ and $R^{18}$, $R^{11}$ and $R^{16}$, $R^{16}$ and $R^{17}$, $R^{18}$ and $R^{11}$, $R^{13}$ and $R^{14}$, $R^{14}$ and $R^{15}$, $R^{19}$ and $R^{20}$ independently comprise a five or six membered ring and the structures are as described previously;

wherein Z is attached directly or indirectly through a linker arm comprising carbon, sulfur, oxygen, nitrogen, and any combinations thereof and wherein said linker arm is saturated or unsaturated, linear or branched, substituted or unsubstituted, or any combinations thereof;

and wherein any of $R^1$, $R^2$, $R^3$, $R^4$, $R^5$, $R^6$, $R^7$, $R^8$, $R^9$ $R^{10}$, $R^{11}$ or $R^{12}$ may further comprise a heteroatom containing side chain, wherein said side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{25}$ and $R^{26}$ and $R^{26}$ and $R^{27}$ independently comprise a five or six membered ring, and wherein any of $R^{25}$, $R^{26}$ or $R^{27}$ may further comprise said heteroatom containing side chain.

In prior art, cyanine dyes have been disclosed that comprise an $SO_3$ group (U.S. Pat. No. 5,268,486, U.S. Pat. No. 5,486,616 and U.S. Pat. No. 5,569,766) but the use of sulfone ($SO_2$) groups to modify the properties of cyanine dyes has not been disclosed. The addition of a sulfonamide group to a cyanine dye has been previously disclosed but only in the context of being part of a linker arm (U.S. Pat. No. 6,448,008) thereby being part of the connection between the dye and a terminal reactive group. Cyanine dyes lacking reactive groups, or cyanine dyes with sulfonamide groups in moieties other than the linker arm were not disclosed in the foregoing reference.

In another aspect of the present invention, novel dyes based upon asymmetric cyanine dyes are disclosed. In one embodiment the dyes have the structure:

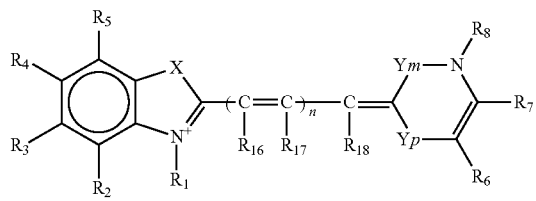

wherein X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 0, 1, 2 or 3;
wherein Y is —$CR^9$=$CR^{10}$—;
wherein m and p can have values of 0 or 1 and m+p=1;

wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);

wherein Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{15}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;

wherein Q(2) comprises a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S and the structures are as described previously;

wherein Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;

wherein $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

wherein $R^{16}$, $R^{17}$, $R^{18}$ and the remaining $R^1$, $R^2$, $R^3$, $R^4$, $R^5$, $R^6$, $R^7$, $R^8$, $R^9$, $R^{10}$, $R^{11}$ and $R^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^2$ and $R^3$, $R^3$ and $R^4$, $R^4$ and $R^5$, $R^6$ and $R^7$, and $R^7$ and $R^8$ may form a 5 or 6 membered ring; or when taken together $R^1$ and $R^{16}$, $R^{11}$, and $R^{16}$, $R^{16}$ and $R^{17}$, $R^{17}$ and $R^{18}$, and $R^{18}$ and $R^9$ may form a 5 or 6 membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S and the structures are as described previously;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein any of $R^1$, $R^2$, $R^3$, $R^4$, $R^5$, $R^6$, $R^7$, $R^8$, $R^9$ or $R^{10}$, $R^{11}$ or $R^{12}$ may further comprise a heteroatom containing side chain wherein said side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

In the prior art, the non-benzazolium portion of asymmetric dyes has been modified with sulfonate groups (U.S. Pat. No. 5,436,134) but not the benzazolium portion as described in the present invention.

In another aspect of the present invention, novel dyes that are based upon xanthine dyes are disclosed. In one embodiment the dyes have the structure:

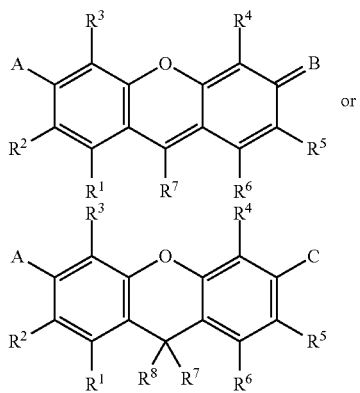

wherein A is $OR^9$ or $NR^{11}R^{12}$, where $R^9$, $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together $R^{11}$ and $R^{12}$ form a five or six membered ring;

wherein B, when present, is O or $N^+R^{21}R^{22}$ where $R^{21}$ and $R^{22}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{21}$ and $R^{22}$ form a five or six membered ring;

wherein C, when present, is $OR^{21}$ or $NR^{21}R^{22}$ where $R^{21}$ and $R^{22}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{21}$ and $R^{22}$ form a five or six membered ring;

wherein at least one of $R^1$, $R^2$, $R^3$, $R^4$, $R^5$, $R^6$ $R^7$, $R^8$, $R^9$, $R^{11}$, $R^{12}$, $R^{21}$ or $R^{22}$ comprises Q, wherein Q comprises a sulfoxide ($SOR^{13}$), a sulfone ($SO_2CR^{13}R^{14}R^{15}$), a sulfonamide ($SO_2NR^{13}R^{14}$), a phosphonate ($PO_3^=$), a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, it does not comprise a terminal reactive group or a linker joining the dye to a target molecule;

wherein $R^{13}$, $R^{14}$, $R^{15}$, $R^{19}$, $R^{20}$ and the remaining $R^1$, $R^2$, $R^3$, $R^4$, $R^5$, $R^6$, $R^7$, $R^8$, $R^9$, $R^{11}$, $R^{12}$, $R^{21}$ or $R^{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$, $R^1$ and $R^2$, $R^2$ and $R^9$, $R^2$ and $R^{11}$, $R^9$ and $R^3$, $R^{11}$ and $R^3$, $R^4$ and $R^{21}$, $R^{21}$ and $R^5$, $R^6$ and $R^7$, $R^6$ and $R^7$, or $R^8$ and $R^1$ form a five or six membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein any of R$^1$, R$^2$, R$^3$, R$^4$, R$^5$, R$^6$ R$^7$, R$^8$, R$^9$, R$^{11}$, R$^{12}$, R$^{21}$ or R$^{22}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain.

Coumarin

In another aspect of the present invention, novel dyes that are based upon coumarin dyes are disclosed. In one embodiment the dyes have the structure:

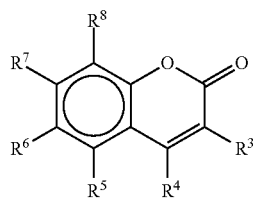

wherein R$^7$ comprises an amine group, a hydroxyl group, or a moiety that can enzymatically be converted into an amine group or hydroxyl group;

wherein at least one of R$^3$, R$^4$, R$^5$, R$^6$, or R$^8$ comprises Q, wherein Q comprises a sulfoxide (SOR$^{13}$), a sulfone (SO$_2$CR$^{13}$R$^{14}$R$^{15}$), a sulfonamide (SO$_2$NR$^{13}$R$^{14}$), a phosphate monoester (PO$_3^-$ER$^{13}$), a phosphate diester (PO$_2$ER$^{13}$ER$^{14}$), a phosphonate monoester (PO$_2^-$ER$^{13}$), a phosphonate diester (POER$^{13}$ER$^{14}$), a thiophosphate (PSO$_3$=), a thiophosphate monoester (PSO$_2^-$ER$^{13}$), a thiophosphate diester (PSOER$^{13}$ER$^{14}$), a thiophosphonate (PSO$_2$=), a thiophosphonate monoester (PSO$^-$ER$^{13}$), a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$), or its thioanalogue (POSR$^{19}$NR$^{13}$R$^{14}$), wherein any of E independently comprises O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, Q does not have a terminal reactive group or a linker arm joining the dye to a target molecule;

wherein R$^{13}$, R$^{14}$, R$^{15}$, R$^{16}$, R$^{17}$, R$^{18}$, R$^{19}$, R$^{20}$ and the remaining R$^3$, R$^4$, R$^5$, R$^6$, or R$^8$ independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together R$^3$ and R$^4$, R$^4$ and R$^5$, and R$^5$ and R$^6$ independently comprise a five or six membered ring;

wherein Z comprises a carboxyl group (CO$_2^-$), a carbonate ester (COER$^{13}$), a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4$=), a phosphate monoester (PO$_3^-$ER$^{13}$), a phosphate diester (PO$_2$ER$^{13}$ER$^{14}$), a phosphonate (PO$_3$=), a phosphonate monoester (PO$_2^-$ER$^{13}$) a phosphonate diester (POER$^{13}$ER$^{14}$), a thiophosphate (PSO$_3$=), a thiophosphate monoester (PSO$_2^-$ER$^{13}$), a thiophosphate diester (PSOER$^{13}$ER$^{14}$), a thiophosphonate (PSO$_2$=), a thiophosphonate monoester (PSO$^-$ER$^{13}$), a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{13}$NR$^{13}$R$^{14}$), or its thioanalogue (POSR$^{19}$NR$^{13}$R$^{14}$), wherein any of E independently comprises O or S;

wherein Z is attached directly or indirectly through a linker arm comprising carbon, sulfur, oxygen, nitrogen, or any combinations thereof and wherein said linker arm is saturated or unsaturated, linear or branched, substituted or unsubstituted, or any combinations thereof;

and wherein any of R$^3$, R$^4$, R$^5$, R$^6$, or R$^8$ may further comprise a heteroatom containing side chain, wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together R$^{25}$ and R$^{26}$ and R$^{26}$ and R$^{27}$ independently comprise a five or six membered ring, and wherein any of R$^{25}$, R$^{26}$ or R$^{27}$ may further comprise said heteroatom containing side chain.

Particularly useful varieties of the novel dyes of the present invention may be based upon 6,8 difluoro-7-hydroxycoumarin as described in U.S. Pat. No. 5,830,912 incorporated herein by reference.

In another aspect of the present invention, novel dyes that are based upon styrene dyes are disclosed. In one embodiment the dyes have the structure:

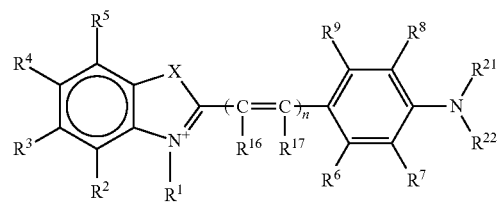

wherein X comprises CR$^{11}$R$^{12}$, NR$^{11}$, O, S or Se where R$^{11}$ and R$^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 1, 2 or 3;

wherein at least one of $R^1$, $R^2$, $R^3$, $R^4$, $R^5$, $R^6$, $R^7$, $R^8$, $R^9$, $R^{11}$, $R^{12}$, $R^{21}$ or $R^{22}$ comprises Q, wherein Q comprises a sulfoxide (SOR$^{13}$), a sulfone (SO$_2$CR$^{13}$R$^{14}$R$^{15}$), a sulfonamide (SO$_2$NR$^{13}$R$^{14}$), a phosphonate (PO$_3$=), a phosphonate monoester (PO$_2^-$ER$^{13}$) a phosphonate diester (POER$^{13}$ER$^{14}$), a thiophosphate (PSO$_3$=), a thiophosphate monoester (PSO$_2^-$ER$^{13}$) a thiophosphate diester (PSOER$^{13}$ER$^{14}$), a thiophosphonate (PSO$_2$=), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) wherein any of E can independently comprise O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q(2) is a sulfonamide, it does not comprise a terminal reactive group or a linker joining the dye to a target molecule;

wherein $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

wherein $R^{16}$, $R^{17}$ and the remaining $R^1$, $R^2$, $R^3$, $R^4$, $R^5$, $R^6$, $R^7$, $R^8$, $R^9$, $R^{11}$, $R^{12}$, $R^{16}$, $R^{17}$, $R^{21}$ and $R^{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^2$ and $R^3$, $R^3$ and $R^4$, $R^4$ and $R^5$, $R^6$ and $R^7$, $R^7$ and $R^8$, $R^1$ and $R^{16}$, $R^{11}$ and $R^{16}$, $R^{16}$ and $R^{17}$, $R^{17}$ and $R^{18}$, and $R^{18}$ and $R^9$ may form a 5 or 6 membered ring;

wherein Z comprises a carboxyl group (CO$_2^-$), a carbonate ester (COER$^{13}$), a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4$=), a phosphate monoester (PO$_3^-$ER$^{13}$), a phosphate diester (PO$_2$ER$^{13}$ER$^{14}$), a phosphonate (PO$_3$=) a phosphonate monoester (PO$_2^-$ER$^{13}$) a phosphonate diester (POER$^{13}$ER$^{14}$), a thiophosphate (PSO$_3$=), a thiophosphate monoester (PSO$_2^-$ER$^{13}$) a thiophosphate diester (PSOER$^{13}$ER$^{14}$), a thiophosphonate (PSO$_2$=), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^4$, $R^5$, $R^6$, $R^7$, $R^8$, $R^9$, $R^{11}$, $R^{12}$, $R^{21}$ or $R^{22}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain.

In another embodiment of the present invention, the styryl dye comprises a picoline or quinoline moiety instead of a benzazolium group. As such, these dyes have the structure:

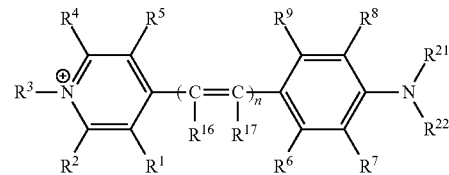

wherein n can be 1, 2 or 3;

wherein at least one of $R^1$, $R^2$, $R^3$, $R^4$, $R^5$, $R^6$, $R^7$, $R^8$, $R^9$, $R^{21}$ or $R^{22}$ comprises Q wherein Q comprises a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4$=), a phosphate monoester (PO$_3^-$ER$^{13}$), a phosphate diester (PO$_2$ER$^{13}$ER$^{14}$), a phosphonate (PO$_3$=) a phosphonate monoester (PO$_2^-$ER$^{13}$) a phosphonate diester (POER$^{13}$ER$^{14}$), a thiophosphate (PSO$_3$=), a thiophosphate monoester (PSO$_2^-$ER$^{13}$) a thiophosphate diester (PSOER$^{13}$ER$^{14}$), a thiophosphonate (PSO$_2$=), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, it does not comprise a terminal reactive group or a linker joining the dye to a target molecule;

wherein $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

wherein $R^{16}$, $R^{17}$ and the remaining $R^1$, $R^2$, $R^3$, $R^4$, $R^5$, $R^6$, $R^7$, $R^8$, $R^9$, $R^{21}$ or $R^{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^1$ and $R^2$, $R^2$ and $R^3$, $R^3$ and $R^4$, $R^4$ and $R^5$, $R^5$ and $R^{16}$, $R^{16}$ and $R^{17}$, $R^{17}$ and $R^9$, $R^9$ and $R^8$, $R^8$ and $R^{21}$, $R^{21}$ and $R^{22}$, $R^{22}$ and $R^7$, and $R^7$ and $R^6$ may form a 5 or 6 membered ring;

wherein Z comprises a carboxyl group (CO$_2^-$), a carbonate ester (COER$^{13}$), a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4$=), a phosphate monoester (PO$_3^-$ER$^{13}$), a phosphate diester (PO$_2$ER$^{13}$ER$^{14}$), a phosphonate (PO$_3$=) a phosphonate monoester (PO$_2^-$ER$^{13}$) a phosphonate diester (POER$^{13}$ER$^{14}$), a thiophosphate (PSO$_3$=), a thiophosphate monoester (PSO$_2^-$ER$^{13}$) a thiophosphate diester (PSOER$^{13}$ER$^{14}$), a thiophosphonate (PSO$_2$=), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$R$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of R$^1$, R$^2$, R$^3$, R$^4$, R$^5$, R$^6$, R$^7$, R$^8$, R$^9$, R$^{21}$ or R$^{22}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain.

When R$^4$ and R$^5$ comprise alkyl chains that are joined together, a quinoline moiety can be formed, the dye thereby having the structure:

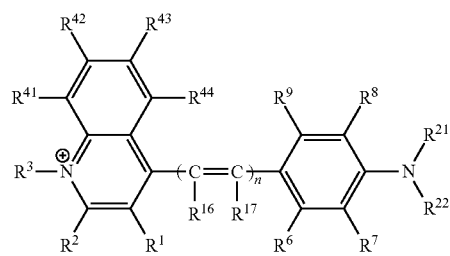

Where R$^{41}$, R$^{42}$, R$^{43}$ and R$^{44}$ are as described previously for R$^1$, R$^2$, R$^3$, R$^4$, R$^5$, R$^6$, R$^7$, R$^8$, R$^9$, R$^{21}$ and R$^{22}$.

Complex Ring Structures

As described above some of the R groups may be joined together to form one or more fused 5 or 6 membered ring structures. It is understood that the complex rings that are formed by closure of R groups may be further substituted with any of the R groups described previously. Examples of complex rings that may be formed for the benzazolium portion of cyanine and asymmetric cyanine dyes can comprise but not be limited to:

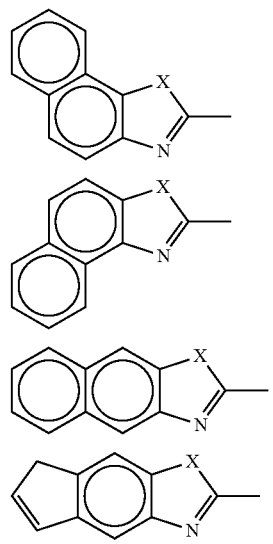

In addition, "rigid" cyanine dyes have been described where a fused ring is formed where the nitrogen of the benzazolium is linked to the nearest carbon of the methine bridge (U.S. Pat. No. 6,133,445 and U.S. Pat. No. 6,686,145 both of which are hereby incorporated by reference). Similarly in a cyanine dye with a monomethine bridge (i.e. when n=0), a rigid linkage can be formed by joining the nitrogens of the benzazolium group to each other (U.S. Pat. No. 5,852,191 and U.S. Pat. No. 5,981,747 both of which are incorporated by reference).

If desired, a variation of the preceding dyes can be the substitution of an azabenzazolium instead of a benzazolium moiety in the cyanine, asymmetric cyanine and styrene dyes; i.e. a Nitrogen replaces the carbon in the positions where R$^2$, R$^3$, R$^4$, R$^5$, R$^7$, R$^8$, R$^9$ or R$^{10}$ are connected to the benzazolium moiety of cyanine dyes or to the R$^2$, R$^3$, R$^4$ or R$^5$ positions of the asymmetric cyanine and styrene dyes disclosed previously. Methods for the synthesis and use of an azabenzazolium based dyes are disclosed in U.S. Pat. No. 6,664,047 B1, hereby incorporated by reference. As such these moieties would have the structures:

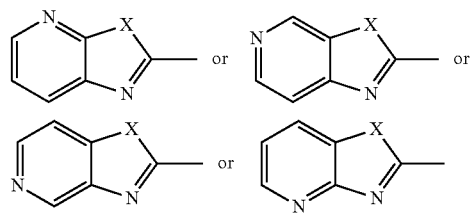

Examples of rings and complex rings that may comprise the non-benzazolium portion of an asymmetric cyanine dye can comprise but not be limited to:

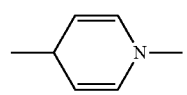

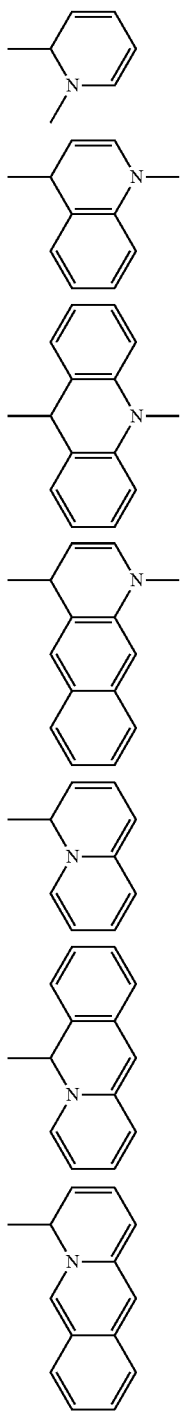

Examples of rings and complex rings that may be part of the non-benzazolium portion of a styryl dye can comprise but not be limited to:

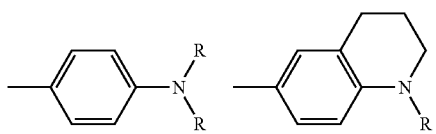

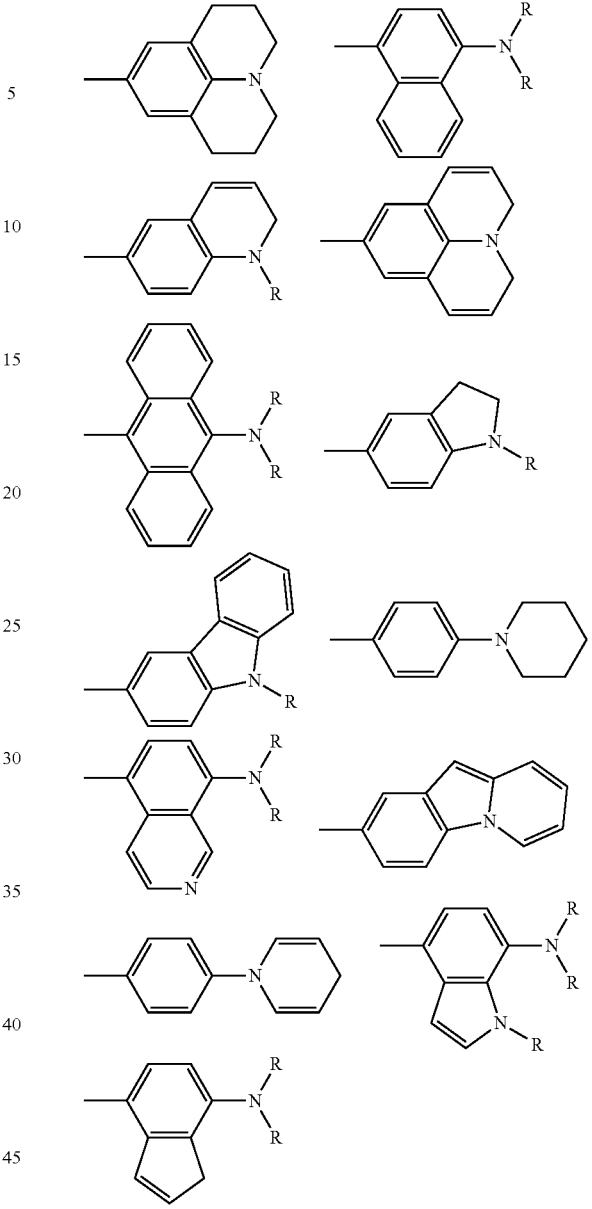

Reactive Groups and Targets

In another aspect of the present invention, one of the R groups is a reactive group thereby allowing the dyes of the present invention to be attached to a useful target molecule. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use with the present invention; examples can include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group. Use of a terminal alkene or alkyne groups for attachment of markers has been previously described in U.S. Patent Application Ser. No. 2003/0225247, hereby incorporated by reference. The use of platinum coordinate groups for attachment of other dyes has been previously disclosed in U.S. Pat. No. 5,580,990 and the use of alkyl groups has been previously described in U.S. Pat. No. 6,593,465 both of which are hereby incorporated by reference.

Examples of useful target molecules can include but not be limited to a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, glycolipid, viral particle, viral component, bacterial cell, bacterial component, eucaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof.

The nucleoside, nucleotide, oligonucleotide, or polynucleotide can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues and any combination thereof.

As described above, the dyes of the present invention may have dyes as targets thereby creating composite dyes. By joining the dyes of the present invention to another dye, unique properties may be enjoyed that are not present in either dye alone. For instance, if one of the dyes of the present invention is joined to another dye such that it creates an extended conjugation system, the spectral characteristics of the dye may be different than either dye component. Another example of this method is where the conjugation systems do not overlap but the proximity allows an internal energy transfer to take place thereby extending the Stokes shift. For an example of this, see U.S. Pat. No. 5,401,847, U.S. Pat. No. 6,008,373 and U.S. Pat. No. 5,800,996 all of which are hereby incorporated by reference. Other properties may also be enhance by this joining, for example, it has been previously described that the joining together of two ethidium bromide molecules generates a dye that has enhanced binding to nucleic acids (U.S. Patent Application Serial No. 2003/0225247, hereby incorporated by reference). Other composite dyes have been described that simultaneously enjoy both properties, i.e. enhanced binding and energy transfer (U.S. Pat. No. 5,646,264 hereby incorporated by reference). Furthermore, these composites dyes are not limited to binary constructs of only two dyes, but may comprise oligomeric or polymeric dyes. These composite dyes may be comprised of the same dye or different dyes may be joined together depending upon the properties desired.

Utility may also be achieved by attaching a dye of the present invention to a target specific moiety. Thus, binding between the target specific moiety and its corresponding target may be monitored by essentially determining the presence or amount of dye that is bound to the target. Well-known examples of such assays are hybridizations between complementary nucleic acids as well as binding that takes place between antibodies and their corresponding antigens. Other binding pairs that may be of interest can include but not be limited to ligand/receptor, hormone/hormone receptor, carbohydrate/lectin and enzyme/substrate. Assays may be carried out where one component is fixed to a solid support and a corresponding partner is in solution. By binding to the component fixed to the support, the partner now becomes attached to the support as well. A well-known example of this method is the microarray assays where labeled analytes become bound to discrete sites on the microarray. Homogeneous probe dependent assays are also well known in the art and may take advantage of the present invention. Examples of such methods are energy transfer between adjacent probes (U.S. Pat. No. 4,868,103), the Taqman exonuclease assay (U.S. Pat. No. 5,538,848 and U.S. Pat. No. 5,210,015), Molecular Beacons (U.S. Pat. No. 5,118,801 and U.S. Pat. No. 5,925,517) and various real time assays (U.S. patent application Ser. No. 10/096,076), all of which are incorporated by reference.

Antibodies labeled with dyes of the present invention may be used in various formats. For example, an antibody with one of the dyes of the present invention may be used in an immunofluorescent plate assay or in situ analysis of the cellular location and quantity of various antigenic targets. Antibodies labeled with dyes may also be used free in solution in cell counting or cell sorting methods that use a flow cytometer.

The presence or absence of a signal may then be used to indicate the presence or absence of the target itself. An example of this is a test where it is sufficient to know whether a particular pathogen is present in a clinical specimen. On the other hand, quantitative assays may also be carried out where it is not so much the intention of evaluating if a target is present but rather the particular amount of target that is present. An example of this is the previously cited microarray assay where the particular rise or fall in the amount of particular mRNA species may be of interest.

In another embodiment of the present invention, dyes that have been disclosed above as well as dyes described previous literature may be attached to a carrier with a more general affinity. Dyes may be attached to intercalators that in themselves do not provide signal generation but by virtue of their binding may bring a dye in proximity to a nucleic acid. A further example is attachment of dyes to SDS molecules thereby allowing dyes to be brought into proximity to proteins. Thus this embodiment describes the adaptation of a dye or dyes that lack affinity to a general class of molecules may be adapted by linking them to non-dye molecules or macromolecules that can convey such properties.

The dyes of the present invention may also be used without tethering them to a target specific moiety. For example, it has long been known that ethidium bromide has a high affinity for binding to double-stranded DNA. For many years this has been a standard method of identifying and characterizing nucleic acids that have been separated by molecular weights after electrophoresis in a gel. An additional useful property of ethidium bromide that has been exploited in such gel assays is the heightened fluorescence that takes place after ethidium has bound to a double-stranded nucleic acid molecule. A similar effect has been seen for stains that can increase fluorescence or even change emission wavelengths after binding to proteins (See Chapter 9.1 in "Handbook of Molecular Probes and Research Chemicals" $6^{th}$ edition, 1996, Molecular Probes, Inc. Eugene, Oreg., incorporated hereby by reference), These stains may be relatively specific for particular macromolecules or they may have a more general affinity. For instance a cyanine based dye "Stains all" has been used for staining nucleic acids, proteins, polysaccharides and lipids (Green 1975 J Histochem Cytochem 23; 411-423, Kelly and Parker, 1981 J Bact 145; 1018-1024). The effects of interactions of this dye can be seen by the production of various colors depending upon the nature of the substance bound to the dye i.e. DNA is blue, RNA is bluish purple and proteins are generally pink or reddish although there are variations for individual proteins.

Various applications may enjoy the benefits of binding the dyes of the present invention to appropriate targets. As described above, staining of macromolecules in a gel is a methodology that has a long history of use. More recent applications that also may find use are real time detection of amplification (U.S. Pat. No. 5,994,056, U.S. Pat. No. 6,174,670 and U.S. patent application Ser. No. 10/096,076, all of which are hereby incorporated by reference), and binding of nucleic acids to microarrays. In situ assays may also find use where the binding of dyes of the present invention is used to identify the location or quantity of appropriate targets.

It is also a subject of the present invention that the dyes of the present invention as well as dyes that have been described previously in the literature may be joined together to create composite dyes with multiple binding properties. For instance, a dye that has an affinity for nucleic acids can be joined to a dye that has an affinity for proteins, thereby creating a composite dye that has an affinity for both nucleic acids and proteins. If the particular affinities of these dyes are strong, the multiple binding dye will have an expanded range of use contributed by the properties of each of the individual affinities. Thus for instance, a dye with an affinity for nucleic acids and a lack of affinity for proteins may be joined to a dye with an affinity for proteins and a lack of affinity for nucleic acids to create a multiple binding dye with affinities for both nucleic acids and proteins. On the other hand, two dyes may be chosen that each have a discrete but low affinity for their targets, where the composite dye has an overall higher affinity of binding (i.e cooperative binding) when each of the targets is in proximity to each other. In the present invention, the targets are comprised of different types of macromolecules, and as such the components of the composite dyes have heterogeneous affinities. Thus for example, a dye that has an affinity for lipids joined to a dye that has an affinity for proteins may create a co-operative binding dye that has a higher affinity for proteins in cell membranes. In another example, a dye with an affinity for proteins joined to a dye with an affinity for nucleic acids may create a co-operative binding dye with a special affinity for proteins associated with or bound to nucleic acids. In a preferred embodiment, one or both dyes have enhanced fluorescence upon binding to their appropriate targets. The detection of binding of such dyes can enjoy energy transfer, quenching, changes in wavelength or even a mixture of color emissions.

It should be pointed out that a composite product with affinities for two different groups does not need to have dyes in each of the components. The major principle is that the binding event is dependent upon the simultaneous presence of both targets. Thus for example, a non-fluorescent compound that binds to a particular target can be combined with a fluorescent dye that has an affinity for a different target and resultant co-operative binding dye can exhibit enhanced signaling when each of the targets are in proximity to each other. Furthermore, in addition to being neutral in terms of having an absence of fluorescent signal capability, one of the partners may be of a negative nature, i.e a fluorescence quencher. Thus for instance, when the multiple binding dye is in free in solution due to a lack of targets, the quencher in one component effectively inhibits fluorescence in the other component. However, simultaneous binding of the dye to each of the different target types can result in a loss of the quenching. An example of a system with a single binding affinity that has been previously mentioned is the Molecular Beacon method, where binding of the probe to its appropriate target causes a physical separation of a quencher and a fluorescent moiety thereby generating a binding dependent signal.

It should also be understood that it is not a necessity for each of the components to have a single affinity thereby creating a composite multiple binding dye with only two affinities. Again, to use the examples described previously, a dye with a high affinity for nucleic acids and a low affinity for lipids can be joined to a dye with a high affinity for proteins to produce a multiple binding dye with high affinities for both proteins and nucleic acids. In a similar fashion, a dye with a low affinity for nucleic acids may be joined to a dye with a low affinity for both proteins and lipids thereby creating a multiple binding dye that may have a co-operative affinity for both protein/nucleic acid complexes and for nucleic acid/membrane complexes.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Synthesis of Dye 101

(a) Preparation of 7-Formyl julolidine (Compound 1)

A solution of julolidine (15.0 g, 86.6 mmol) in DMF (100 ml) was cooled in an ice bath. While vigorously stirring this solution, $POCl_3$ (20.0 g, 129.8 mmol) was added drop wise. After the addition of $POCl_3$ was complete, the ice bath was removed and the reaction mixture was stirred at room temperature for 30 minutes. An aqueous solution of sodium acetate (25% w/w, 20 ml) was then added to the reaction mixture and it was heated in an oil bath (T=110° C.) for 10 min. The reaction mixture was cooled and poured into ca. 500 ml water and extracted with ethyl acetate. The organic layer was washed twice with water followed by brine, dried over sodium sulfate and then evaporated to dryness to yield 12.0 g of a light yellow solid (Compound 1) with the structure given below:

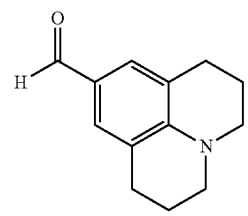 [SMILES: O=Cc1cc2c3c(c1)CCCN3CCC2]

(b) Preparation of 2-methylbenzothiazole-6-sulfonyl chloride (Compound 2)

Chlorosulfonic acid (20 ml, 335.0 mmol) was cooled in an ice bath and 2-methylbenzothiazole (10.0 g, 67.0 mmol) was carefully added drop wise over a period of 30 minutes. The combined mixture was heated at 115-120° C. for 15 hours and after cooling, the mixture was added very slowly to ca. 200 ml ice/water mix. A sticky white solid separated which was extracted into chloroform (300 ml). The organic layer was washed with water (2×, 350 ml), washed with brine (2×, 350 ml), dried and evaporated to yield 11.2 g (67%) of a colorless oil (Compound 2) which solidified upon cooling, $R_f$=0.5 (30% ethyl acetate in hexane). The structure of Compound 2 is given below:

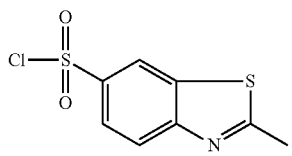

(c) Preparation of N-(2-methylbenzothiazole-6-sulfonyl)piperidine (Compound 3)

A solution of Compound 2 (2.5 g, 10 mmol) in chloroform (15 ml) was added drop wise to a solution of piperidine (1.7 g, 20.0 mmol) in chloroform (10 ml). The combined mixture was stirred at room temperature for 1 hour. The reaction mixture was then washed with water (2×, 50 ml) and brine (1×, 50 ml). The organic layer was dried with sodium sulfate and evaporated. The sticky white solid thus obtained was dissolved in ca. 5 ml of hot ethyl acetate and this solution was then slowly added to 40 ml hexane. The white solid that precipitated was collected, washed with hexane and dried to yield 2.2 g (74%) of Compound 3, $R_f$=0.28 (30% ethyl acetate in hexane). The structure of Compound 3 is given below:

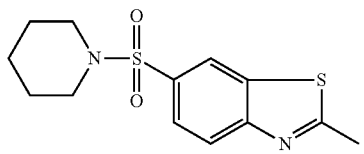

(d) Preparation of N-(2,3-dimethylbenzothiazole-6-sulfonyl)piperidine tosylate (Compound 4)

A mixture of Compound 3 (1.0 g, 3.4 mmol) and p-toluenesulfonic acid methyl ester (0.94 g, 5.1 mmol) was heated in a pressure tube at 130° C. for 1 hour. The mixture was allowed to cool to room temperature, and the resulting mass was triturated with acetone (25 ml) until a gray colored solid separated. The solid was collected by centrifugation, washed with acetone and dried under vacuum to yield 1.4 g (86%) of Compound 4 whose structure is given below:

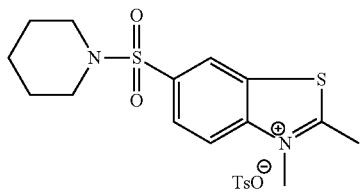 [SMILES: Cc1sc2cc(S(=O)(=O)N3CCCCC3)ccc2[n+]1C]

(e) Preparation of Dye 101

A mixture of Compound 1 (0.19 g, 0.93 mmol), Compound 4 (0.30 g, 0.62 mmol) and piperidine (92 µL, 0.93 mmol) was heated in glacial acetic acid (3 ml) at 115-120° C. for 2 hours. The reaction mixture was cooled to room temperature and mixed with 30 ml isopropanol. This combined mixture was added drop wise to 300 ml hexane and the dark purple solid precipitate was collected and dried to yield 0.4 g (yield: 96%) of Dye 101. Abs (max, in methanol)=588 nm; Em=624 nm, $\epsilon$=90,580 M$^{-1}$ cm$^{-1}$. The structure of this dye is as follows:

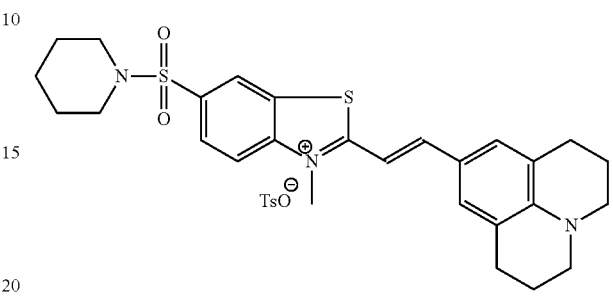

Example 2

Synthesis of Dye 102

(a) Preparation of N-(6-carboxyl hexane)-2,3,4 tetrahydro quinoline (Compound 5)

A mixture of 1,2,3,4 tetrahydro quinoline (10.0 g, 75.0 mmol), 6-bromo-hexanoic acid (21.9 g, 112.5 mmol) and triethyl amine (11.4 g, 112.5 mmol) in 50 ml ethanol was refluxed for 16 hours. The reaction mixture was cooled and precipitated. The precipitate was then collected by filtration. The remaining solvents were removed in a rotary evaporator and to the residue thus obtained 200 ml ethyl acetate and 200 ml water was added. The organic layer was separated, washed with water and brine, dried over sodium sulfate and evaporated to dryness to yield 20.0 g of a dark brown oil (Compound 5) with the structure given below.

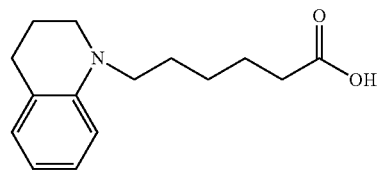 [SMILES: O=C(O)CCCCCN1CCCc2ccccc21]

(b) Preparation of N-(6-carboxyl hexane)-2,3,4 tetrahydro-7-formyl quinoline (Compound 6)

This procedure was carried out as described previously in step (a) of Example 1, with POCl$_3$ (4.7 g, 30.3 mmol) and DMF (40 ml) and using compound Compound 5 (5.0 g, 20.7 mmol) instead of the julolidine used in step (a) of Example 1. Compound 6 was obtained as a dark liquid (3.46 g) and used without any further purification. The structure of Compound 6 is given below:

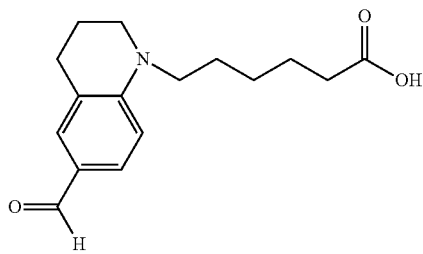 [SMILES: O=Cc1ccc2c(c1)CCCN2CCCCCC(=O)O]

(c) Preparation of Dye 102

The procedure was carried out as described previously in step (e) of Example 1 with Compound 4 (0.24 g, 0.5 mmol), piperidine (72 μL, 0.73 mmol) and glacial acetic acid (2 ml) and substituting Compound 6 (0.2 g, 0.73 mmol) in place of the Compound 1 used in Example 1. The resultant Dye 102 was obtained as a dark purple solid (0.25 g, yield: 68%). The structure of Dye 102 is given below:

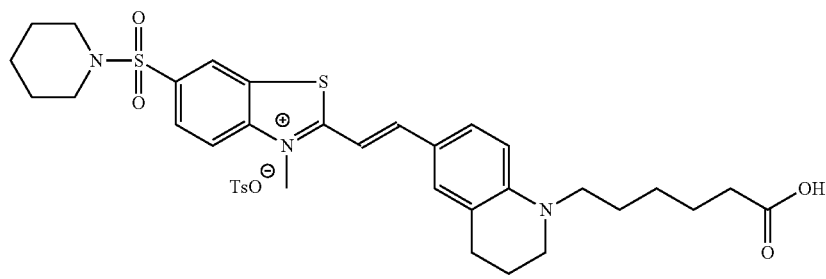 [SMILES: C[n+]1c(/C=C/c2ccc3c(c2)CCCN3CCCCCC(=O)O)sc2cc(S(=O)(=O)N3CCCCC3)ccc21]

Example 3

Synthesis of Dye 103

(a) Preparation of N-[N'-(4'-Sulfobutyl)-2-methyl-benzothiazole-6-sulfonyl)piperidine, Inner Salt (Compound 7)

A mixture of Compound 3 (1.0 g, 3.4 mmol) (from step (c) of Example 1) and 1-4-butane sultone (0.55 g, 4.0 mmol) was heated in a pressure tube at 140-145° C. for 3 hours. The mixture was allowed to cool to room temperature, and the resulting mass was triturated with acetone (40 ml) until a pink solid separated. The solid was collected by centrifugation, washed with acetone and dried under vacuum to yield 0.21 g (14%) of Compound 7 with the structure:

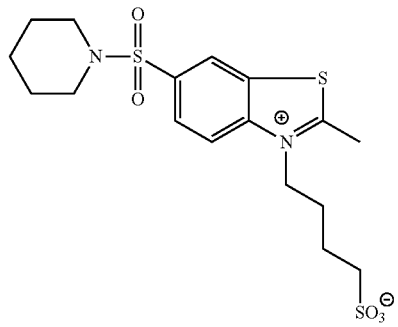

(b) Preparation of Dye 103

A mixture of compound 7 (0.20 g, 0.46 mmol), 9-ethyl-3-carbazolecarboxaldehyde (0.11 g, 0.50 mmol) and piperidine (20 μL, 0.2 mmol) was refluxed in ethanol (2 ml) for 18 hours. The reaction mixture was cooled to room temperature and mixed with 20 ml ethyl acetate. The precipitated solid was collected by centrifugation, washed with ethyl acetate (2×25 ml) and dried under vacuum to yield 0.27 g of an orange brown solid (Dye 103). For spectral analysis, a small amount (~40 mg) of Dye 103 was purified on a silica column using a stepwise gradient of methanol (5% to 15%) in chloroform. Abs (max, methanol)=503 nm; Em=596 nm, $\epsilon$=30,000 $M^{-1}$ $cm^{-1}$. The structure of Dye 103 is given below:

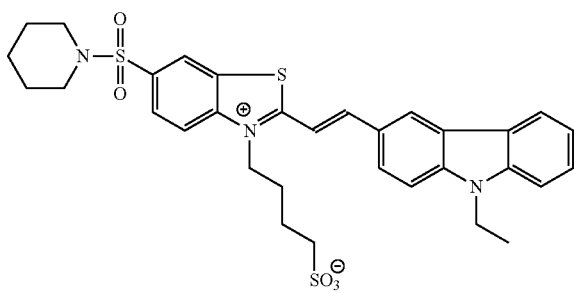

Example 4

Synthesis of Dye 104

This process was carried out as described previously in step (b) of Example 3, using 9-ethyl-3-carbazolecarboxaldehyde (0.10 g, 0.45 mmol), piperidine (18 μL, 0.18 mmol) and ethanol (3 ml) but in this procedure, Compound 4 (0.2 g, 0.41 mmol) from step (d) of Example 1 was used instead of the Compound 7 used in Example 3. The resultant Dye 104 was precipitated using ethyl ether, as a brown solid (0.23 g, yield: 81%). The structure of this dye is given below:

Example 5

Synthesis of Dye 105 and its NHS Ester

(a) Preparation of Intermediate

A mixture of Compound 4 (1.0 g, 2.1 mmol) from step (d) of Example 1 and N,N'-diphenylformamidine (0.5 g, 2.5 mmol) in acetic acid (5 ml) was heated and refluxed for 2 hours. The reaction mixture was cooled and added to ethyl ether (45 ml). The precipitated dark colored solid was collected by centrifugation, washed with ether, dried under Argon and immediately used in the next step.

(b) Preparation of Dye 105

The intermediate obtained in step (a) was added to a solution of 1-(ε-carboxypentynyl)-2,3,3-trimethylindoleninium-5-sulfonate (1.3 g, 3.6 mmol) dissolved in a mixture of acetic anhydride (10 ml) and pyridine (10 ml). The combined mixture was stirred in the dark at room temperature for 18 hours. The precipitated solid was collected by centrifugation, washed with a pyridine/acetic anhydride mixture (1:1, 30 ml), washed with ethyl acetate (2×, 30 ml) and dried to yield 0.63 g of a purple solid (Dye 105). Abs (max, in water)=567 nm; Em=580 nm. The structure of Dye 105 is given below:

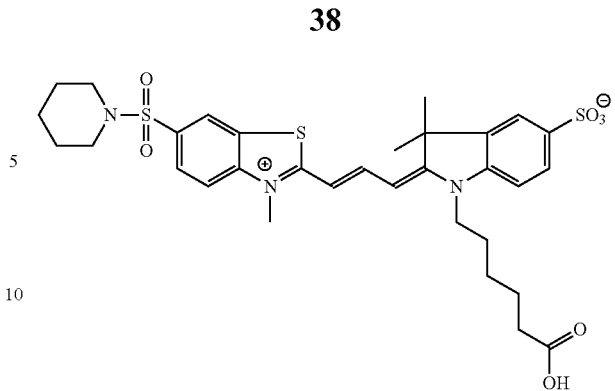

(c) Preparation of NHS Ester of Dye 105

A mixture of Dye 105 (0.5 g, 0.74 mmol), N-hydroxysuccinimide (0.13 g, 1.11 mmol) and DCC (0.23 g, 1.11 mmol) in DMF (2 ml) was stirred at room temperature in the dark for 17 hours. DCC-urea precipitated out and was removed by centrifugation. The supernatant was added drop wise to a 10-fold excess of ethyl acetate. The precipitated dark solid was collected by centrifugation, washed with ethyl acetate and dried to yield 80.0 mg of the NHS ester of Dye 105. The structure of this compound is given below:

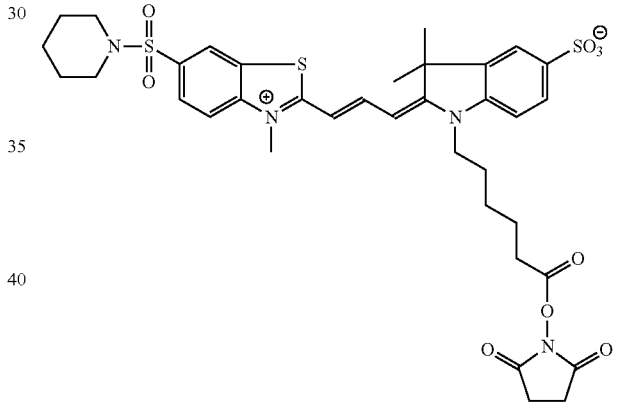

Example 6

Synthesis of Benzoxazole Dyes

The previous examples have been based upon a benzothiazole moiety. A variety of different dyes may also be synthesized that are based upon a benzoxazole moiety instead.

(a) Preparation of 2-methylbenzoxazole-6-sulfonyl chloride (Compound 8)

Chlorosulfonic acid (12.5 ml, 187.8 mmol) was cooled in an ice bath and 2-methylbenzoxazole (5.0 g, 37.5 mmol) was carefully added drop wise over a period of 15 min. The combined mixture was heated at 115-120° C. for 16 hours. After cooling, the mixture was added very slowly to ca. 100 ml ice/water mix. The white solid that separated was collected by filtration, washed with water until washings were neutral and dried to yield 5.2 g (59%) of Compound 8, whose structure is given below:

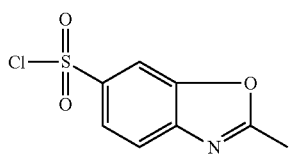

(b) Preparation of N-(2-methylbenzoxazole-6-sulfonyl)piperidine (Compound 9)

Piperidine (2.2 g, 26 mmol) was added drop wise to a solution of Compound 8 (3.0 g, 10 mmol) in chloroform (30 ml) and DMF (10 ml). The combined mixture was stirred at room temperature for 1 hour, and then washed with water (2×, 50 ml) and brine (1×, 50 ml). The organic layer was then dried over sodium sulfate and evaporated to provide 2.76 g (76%) of Compound 9 as a sticky white solid. TLC analysis showed $R_f$=0.25 (30% ethyl acetate in hexane). The structure of this compound is given below:

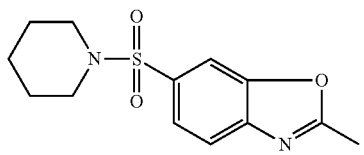 [SMILES: Cc1nc2ccc(S(=O)(=O)N3CCCCC3)cc2o1]

Compound 9 may now be used in the same processes that used (Compound 3) as a reagent to make benzoxazole analogues of Dye 101, Dye 102, Dye 103, Dye 104, Dye 105 as well as other dyes.

Example 7

Synthesis of Dye 106 (NHS Ester of CX2)

(a) Preparation of Compound 10

A mixture of 4-methylpyridine (20 ml) and 6-bromohexanoic acid (10 g) was refluxed overnight. The mixture was cooled to room temperature, and 20 ml of acetone was added. The mixture was stirred at room temperature for 15 minutes followed by addition of 80 ml ether. After filtration, 18 g of a yellow solid (Compound 10) was collected. The structure of Compound 10 is given below:

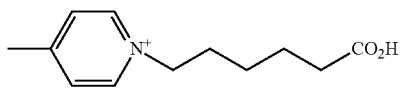

(b) Preparation of Dye 106 from Compound 10

To a solution of 2 g of 1-ethyl-2,3,3,-trimethylindolinium 5-sulfate dissolved in acetic acid (40 ml), 1.6 g of N,N-diphenylformamide was added. The reaction mixture was refluxed for 4 hours and then added drop wise into a stirring mixture of ethyl acetate (25 ml) and ether (25 ml) under argon. The resultant precipitate was collected by centrifugation and added to a solution of 2 g of Compound 10 (prepared in step (a)) dissolved in a mixture of 8 ml of pyridine and 8 ml of acetic anhydride. The reaction mixture was heated to 60-70° C. overnight under argon. After cooling to room temperature, the reaction mixture was added to 200 ml of ethyl acetate. The solution was filtered and the solid residue was dissolved in 50 ml of dry DMF. The DMF was evaporated in vacuum and the residue was dissolved in 50 ml of dry DMF again. To the above solution, 1,3-dicyclohexyl-carbodiimide (5 g) and N-hydroxysuccinimide (5 g) was added. The reaction mixture was stirred at room temperature overnight. Filtration was then used to remove precipitated byproducts. The solution was concentrated by rotary evaporation and the product was purified by silica gel chromatography eluted with 20% methanol in methyl chloride to give 600 mg of a black solid (Dye 106) whose structure is given below:

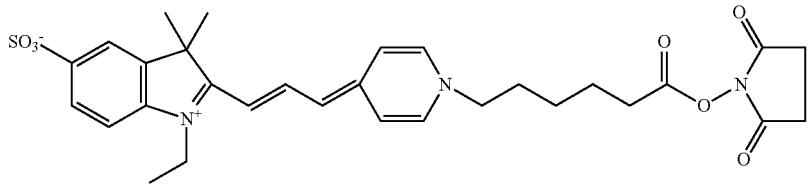

Example 8

Preparation of UTP Labeled with Dye 106

A solution of 58.1 mg of Dye 106 (from Example 7) dissolved in 1 ml of DMF was added to a mixture of allylamine modified UTP (200 µl of 50 µmol/ml solution), KHCO$_3$ (50 mg), 50 µl of 7M LiCl and 5 ml of water. The reaction mixture was stirred at room temperature overnight. After addition of 10 ml of water to the reaction mixture, the solution was extracted with n-BuOH (3×20 ml). The aqueous layer was collected and loaded onto a DEAE-Sephadex column and eluted with a 0.1 M to 0.9 M TEAB gradient. Fractions were checked by HPLC and the appropriate fractions were pooled to give 17 µmol of UTP labeled with Dye 106. The structure of the final product is given below:

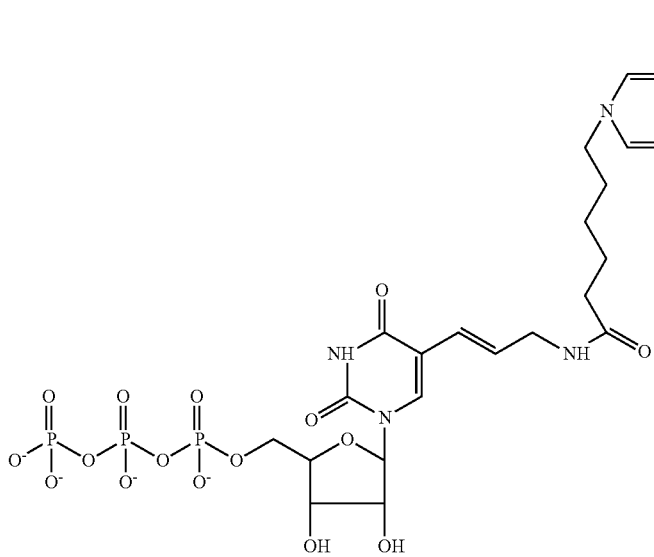

Example 9

Synthesis of Dye 107 (NHS Ester of CX1)

(a) Preparation of Compound 11

Preparation of this compound was carried out essentially as described in step (a) of Example 7 except that 4-methyl quinoline was substituted for the 4-methyl pyridine used in Example 7. The resultant product (Compound 11) has the following structure:

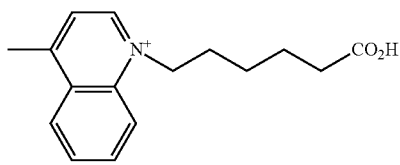 [SMILES: Cc1cc[n+](CCCCCC(=O)O)c2ccccc12]

(b) Preparation of Dye 107 Using Compound 11

To a solution of 8 g of 1-ethyl-2,3,3,-trimethylindolinium 5-sulfonate dissolved in acetic acid (40 ml), 6.6 g of N,N-diphenylformamide was added. The reaction mixture was refluxed for 4 hours and then added dropwise into a stirring mixture of ethyl acetate (150 ml) and ether (150 ml) under argon. The precipitate was collected by centrifugation and added to a solution of 7 g of Compound 11 from step (a) dissolved in a mixture of 50 ml of pyridine and 20 ml of acetic anhydride. The reaction mixture was heated to 60-70° C. for 2 hours under argon. After cooling to room temperature, the reaction mixture was added to 600 ml of ethyl acetate. The solution was filtered and the solid residue was dissolved in 200 ml of dry DMF. The DMF was evaporated in vacuum and the residue was dissolved in 100 ml of dry DMF again. To the above solution, 1,3-dicyclohexyl-carbodiimide (8.86 g) and N-hydroxysuccinimide (10 g) was added. The reaction mixture was stirred at room temperature overnight. After filtration, the solvent was evaporated and the residue was separated by silica gel chromatography eluted with 20% methanol in methyl chloride to give 3.2 g of a black solid (Dye 107) whose structure is given below:

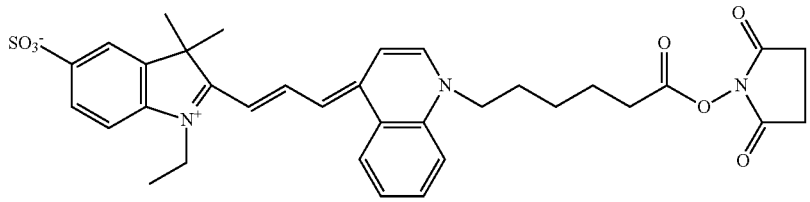

Example 10

Preparation of UTP Labeled with Dye 107

A solution of 62.9 mg of Dye 107 (from Example 9) dissolved in 1 ml of DMF was added to a mixture of allylamine modified UTP (200 µl of 50 µmol/ml solution), KHCO$_3$ (50 mg), 50 µl of 7M LiCl and 5 ml of water. The reaction mixture was stirred at room temperature overnight. After addition of 10 ml of water to the reaction mixture, the solution was extracted with n-BuOH (3×20 ml). The aqueous layer was collected and loaded onto a DEAE-Sephadex column and eluted with a 0.1 M to 0.9 M TEAB gradient. Fractions were checked by HPLC and the appropriate fractions were pooled to give 45.6 μmol of UTP labeled with Dye 107. The structure of the final product is given below:

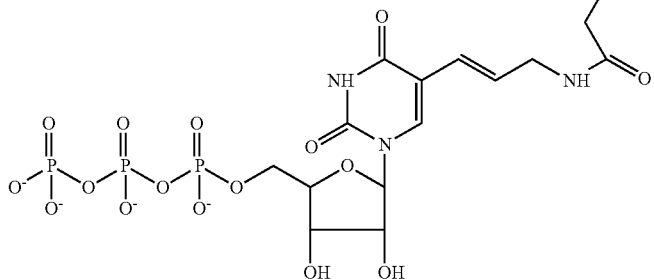

Example 11

Synthesis of Dye 108 (NHS Ester of CX3)

a) Preparation of Compound 12

A mixture of potassium salt of indoleninium sulfonate (8.0 g, 28.8 mmol) and 6-bromohexanoic acid (7.32 g, 37.5 mmol) were heated in a pressure tube at 120-125° C. for 16 hours. The resulting mass was dissolved in boiling DMF (20 mL) and this solution was drop wise added to 200 mL ethyl acetate. The pink solid that precipitated was collected by centrifugation, washed with ethyl acetate and dried under vacuum to yield 21.6 g (89%) of CD-11 with the structure:

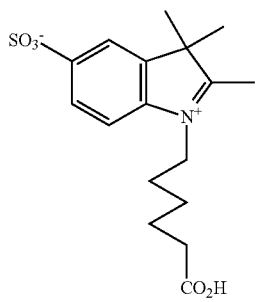

(b) Preparation of Compound 13

Compound 13 was prepared by refluxing ethyl iodide with methyl 6-methylnicotinate. The structure of Compound 13 is shown below:

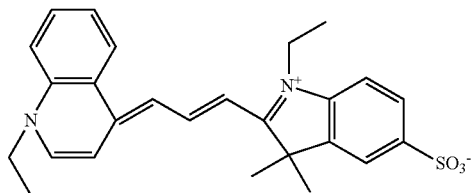

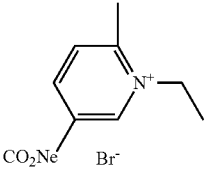

(c) Preparation of Dye 108 Using Compound 12 and Compound 13

To a solution of 1 g of Compound 12 from step (a) dissolved in acetic acid (6 ml), 1 g of N,N-diphenylformamide was added. The reaction mixture was refluxed for 4 hours and then added dropwise into a stirring mixture of ethyl acetate (20 ml) and ether (20 ml) under argon. The precipitate was collected by centrifugation and added to a solution 1.5 g of Compound 13 from step (b) dissolved in a mixture of 10 ml of pyridine and 10 ml of acetic anhydride. The reaction mixture was heated to 60-70° C. for 2 hours under argon. After cooling to room temperature, the reaction mixture was added to 200 ml of ethyl acetate, The solution was filtered and the solid residue was dissolved in 200 ml of dry DMF. The DMF was evaporated in vacuum and the residue was dissolved in 100 ml of dry DMF again. To the above solution, 1,3-dicyclohexyl-carbodiimide (3 g) and N-hydroxysuccinimide (4 g) were added. The reaction mixture was stirred at room temperature overnight. After filtration, the solvent was evaporated and the residue was separated by silica gel chromatography eluted with 20% methanol in methyl chloride to give 0.4 g of a black solid (Dye 107) whose structure is given below.

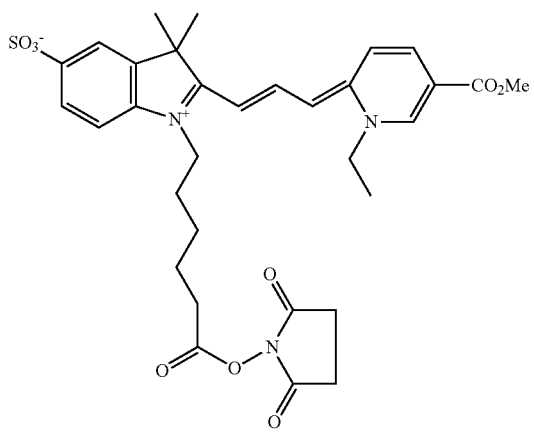

Example 12

Preparation of UTP Labeled with Dye 108

A solution of 100 mg of Dye 107 (from Example 10) dissolved in 5 ml of DMF was added to a mixture of allylamine modified UTP (200 µl of 50 µmol/ml solution), KHCO$_3$ (20 mg), 200 µl of 7M LiCl and 5 ml of water. The reaction mixture was stirred at room temperature overnight. After addition of 10 ml of water to the reaction mixture, the solution was extracted with n-BuOH (3×20 ml). The aqueous layer was collected and loaded onto a DEAE-Sephadex column and eluted with a 0.1 M to 0.9 M TEAB gradient. Fractions were checked by HPLC and the appropriate fractions were pooled to give 86 µmol of UTP labeled with Dye 108. The structure of the final product is given below:

Example 13

Preparation of dUTP Labeled with Dyes

For the preparation of labeled deoxyribonucleotides, the same procedures described in Examples 8, 10 and 12 were carried out except that allylamine modified dUTP was substituted for the allylamine modified UTP.

Example 14

Synthesis of Dye 109 a) Preparation of Compound 14

A mixture of 15 g of 2-(methylthio)benzothiazole and 50 ml of chlorosulfonic acid was heated to 60° C. for 2 hours. After cooling to room temperature, the mixture was slowly added to 300 ml ice water with stirring. The white solid precipitate was collected by filtration and washed with water to give 14 g of Compound 14 whose structure is given below:

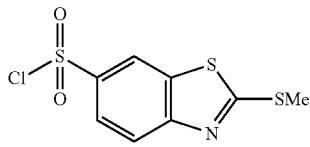

b) Preparation of Compound 15

To a solution of 13.2 g of Compound 14 from step (a) dissolved in 150 ml of dichloromethane, 15 ml of piperidine was slowly added and then the reaction mixture was stirred at room temperature overnight. The reaction mixture was shaken with 50 ml of 2N HCl in a separation funnel followed by the aqueous layer being discarded. The reaction mixture was then shaken with 50 ml of saturated NaHCO$_3$ followed the aqueous layer being discarded and the solution dried over MgSO$_4$. The organic solvent was removed by rotary evaporation and the solid residue Compound 15 was dried in vacuum. The structure of Compound 15 is given below:

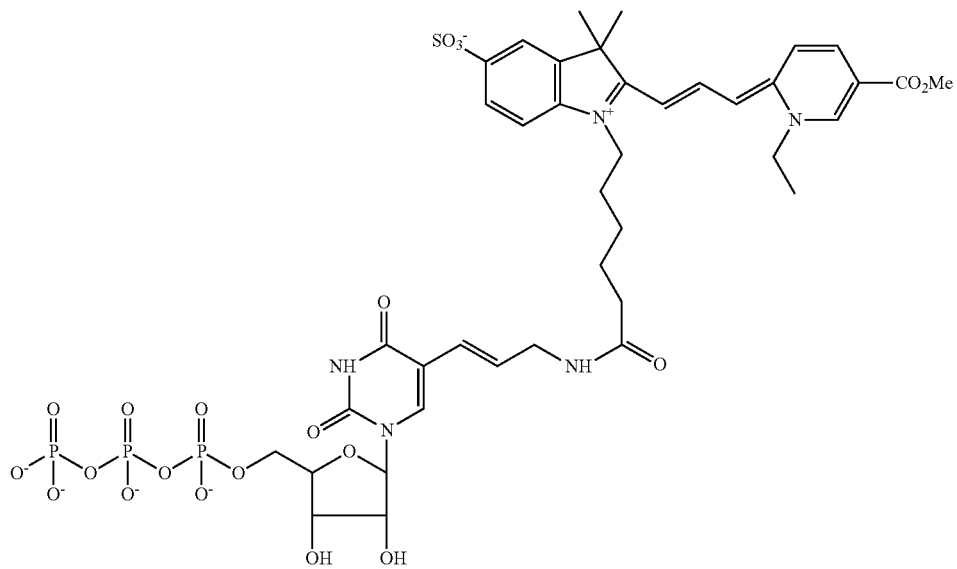

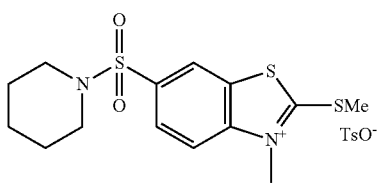

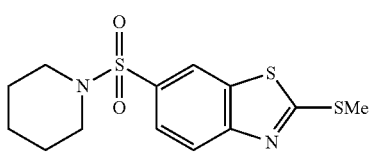 [SMILES: CSc1nc2ccc(S(=O)(=O)N3CCCCC3)cc2s1]

c) Preparation of Compound 16

The crude Compound 15 from step (b) was reacted with 50 ml p-Toluenesulfonic acid methyl ester at 140° C. for 2 hours. After cooling to room temperature, a precipitate formed which was collected by filtration and washed with 50 ml of acetone and 150 ml of ether to give 12 g of Compound 16 whose structure is given below:

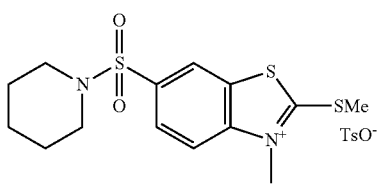

d) Preparation of Compound 17

An intermediate compound, Compound 17, was prepared as described in U.S. Pat. No. 5,658,751 (herein incorporated by reference.). The structure of this compound is given below:

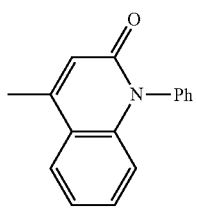 [SMILES: Cc1cc(=O)n(-c2ccccc2)c2ccccc12]

e) Preparation of Compound 18

A mixture of Compound 17 (2.8 g) from step d), $POCl_3$ (1.4 ml), dichloromethane (20 ml) and a catalytic amount DMF (5 μl) was refluxed overnight. The organic solvent was evaporated in vacuum, the residue (Compound 18) was washed with the mixture of ethyl acetate and ether (1:1, 2×50 ml). The structure of Compound 18 is given below:

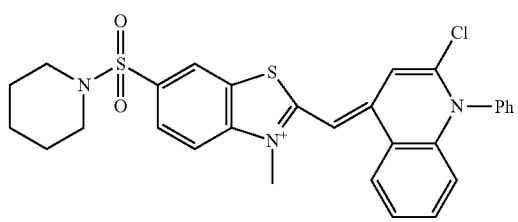 [SMILES: C[n+]1c(/C=C2\C=C(Cl)N(c3ccccc3)c3ccccc32)sc2cc(S(=O)(=O)N3CCCCC3)ccc21]

f) Preparation of Compound 19

Compound 18 from step (e) was dissolved in 40 ml of dichloromethane followed by addition of 4 g of Compound 16 and 1.3 ml of triethylamine. The reaction mixture was stirred at room temperature for 8 hours. The solvent was removed by rotary evaporation and the residue was separated by silica gel chromatography eluted with 10% methanol in methyl chloride to give Compound 19 whose structure is given below:

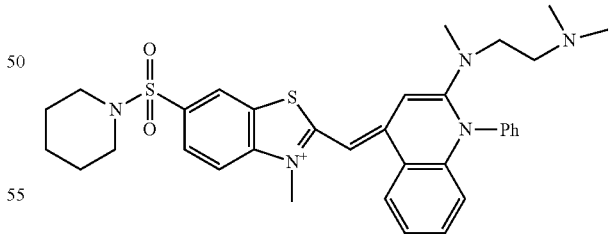

g) Preparation of Dye 109

A mixture of Compound 19 from step f), N,N,N'-trimethylethylenediamine and 1,2-dichloroethane was heated at 55° C. for two hours. The solvent was evaporated and the residue was separated by silica gel chromatography eluted with 10% methanol in methyl chloride to give Dye 109 whose structure is given below:

Example 15

Synthesis of Dye 110

Dye 109 from Example 14 was quarternized by refluxing Dye 109 with excess methyl iodide overnight to give dye 110. The structure of Dye 110 is given below:

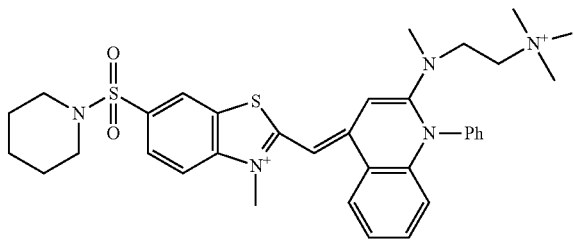 [SMILES: CN(C)CCN(C)C1=C/C(=C\c2sc3cc(S(=O)(=O)N4CCCCC4)ccc3[n+]2C)c2ccccc2N1c1ccccc1]

Example 16

Synthesis of Dye 111

The preparation of Dye 111 was carried out as described in step (g) of Example 14 except that instead of the N,N,N'-trimethylethylenediamine used in Example 14, N-(3-dimethylaminoethyl)-N-propylamine was mixed with Compound 19 and 1,2-dichloroethane. The structure of Dye 111 is as follows:

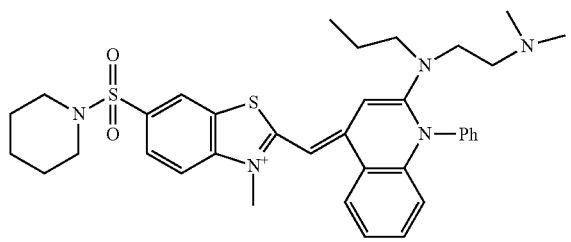

Example 17

Synthesis of Dye 112

Dye 111 from Example 16 was quarternized by refluxing Dye 111 with excess methyl iodide overnight to give Dye 112. The structure of Dye 112 is as follows:

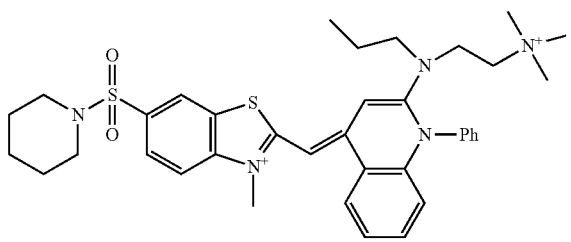 [SMILES: CCCN(CC[N+](C)(C)C)C1=C/C(=C\c2sc3cc(S(=O)(=O)N4CCCCC4)ccc3[n+]2C)c2ccccc2N1c1ccccc1]

Example 18

Synthesis of Dye 113

(a) Preparation of N,N-dihexyl-2-methylbenzo[d]thiazole-6-sulfonamide (Compound 20)

A solution of compound Compound 2 (5.0 g, 20.2 mmol) from step (b) of Example 1 dissolved in chloroform (30 ml) was added drop wise to a solution of dihexylamine (4.5 g, 24.2 mmol) in chloroform (20 ml). The combined mixture was stirred at room temperature for 2 hours. The reaction mixture was then washed with water (2×, 50 ml) and brine (1×, 50 ml). The organic layer was then dried with sodium sulfate and evaporated. The residue thus obtained was suspended in ca. 5 ml hot ethyl acetate and this solution was then slowly added to 40 ml hexane. The white solid that precipitated was filtered and the filtrate evaporated to dryness to provide 7.76 g (97%) of Compound 20 as a syrupy liquid, $R_f$=0.43 (30% ethyl acetate in hexane). The structure of this compound is given below:

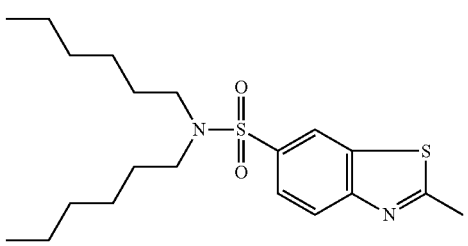 [SMILES: CCCCCCN(CCCCCC)S(=O)(=O)c1ccc2nc(C)sc2c1]

(b) Preparation of 6-(N,N-dihexylsulfamoyl)-2,3-dimethylbenzo[d]-thiazole-3-ium tosylate (Compound 21)

A mixture of Compound 20 (2.0 g, 5.0 mmol) and p-toluenesulfonic acid methyl ester (1.4 g, 7.5 mmol) was heated in a pressure tube at 130° C. for 2 hours. The mixture was allowed to cool to room temperature, and the resulting mass was dissolved in ethyl acetate (4 ml). The combined mixture was then added drop wise to hexane (40 ml). A sticky dark brown solid separated which was washed with hexane and dried under vacuum to yield 2.3 g (78%) of Compound 21 which was used without any further purification. The structure of this compound is given below:

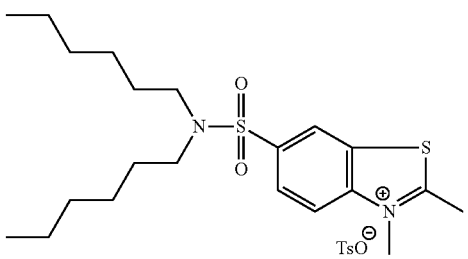

(c) Preparation of 4-(dihexylamine) benzaldehyde (Compound 22)

This procedure was similar to the one described earlier in step (a) of Example 1, except using N,N-di-N-hexylaniline (5.0 g, 19.1 mmol), POCl$_3$ (4.5 g, 28.7 mmol) and DMF (55 ml). Compound 22 was obtained as a light green liquid (5.06 g) and used without any further purification. $R_f$=0.15 (5% ethyl acetate in hexane). The structure of this compound is given below:

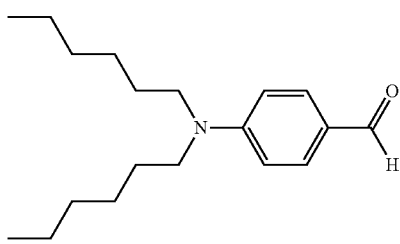 [SMILES: CCCCCCN(CCCCCC)c1ccc(C=O)cc1]

(d) Preparation of Dye 113

A mixture of Compound 21 (0.50 g, 0.9 mmol), Compound 22 (0.30 g, 1.0 mmol) and piperidine (40 µL, 0.4 mmol) was refluxed in ethanol (5 ml) for 18 hours. The reaction mixture was cooled to room temperature and mixed with 10 ml ethyl ether and the combined mixture was added to 100 ml hexane. The precipitated solid was collected by centrifugation, washed with hexane (2×25 ml) and dried under vacuum to yield 0.26 g of a purple solid (Dye 113). Abs (max, methanol) =557 nm; Em=595 nm, $\epsilon$=75,000 $M^{-1}$ $cm^{-1}$. The structure of Dye 113 is given below:

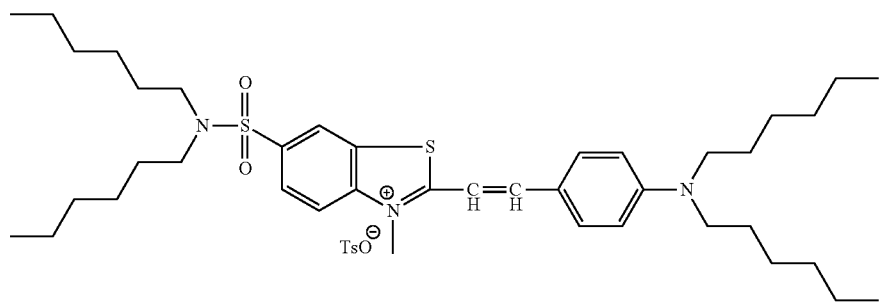

Example 19

Synthesis of Dye 114

A mixture of compound Compound 7 (0.17 g, 0.4 mmol) from step (a) of Example 3, Compound 22 (0.13 g, 0.44 mmol) from step (c) of Example 18 and piperidine (17 µL, 0.18 mmol) was refluxed in ethanol (2 ml) for 18 hours. The reaction mixture was cooled to room temperature and mixed with 30 ml ethyl ether. The precipitated solid was collected by centrifugation, washed with ethyl ether (2×25 ml) and dried under vacuum to yield 0.23 g (83%) of a dark purple solid (Dye 114). Abs (max, methanol)=562 nm. The structure of Dye 114 is given below:

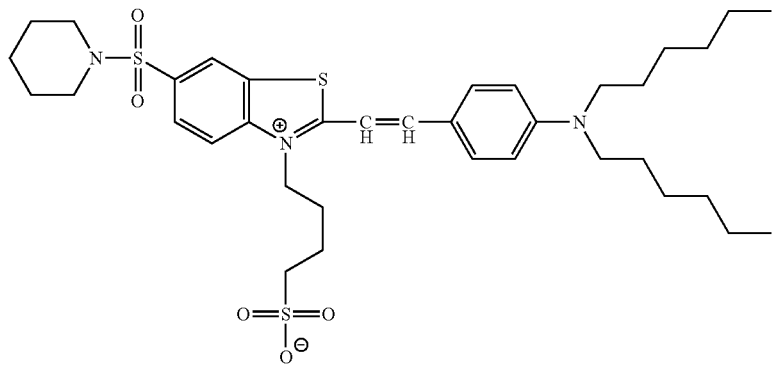 [SMILES: CCCCCCN(CCCCCC)c1ccc(C=Cc2sc3cc(S(=O)(=O)N4CCCCC4)ccc3[n+]2CCCCS(=O)(=O)[O-])cc1]

Example 20

Synthesis of Dye 115

(a) Preparation of Ethyl 3-(4-methylquinolinium-1-yl)propylphosphonate (Compound 23)

A mixture of lepidine (1.0 g, 7.0 mmol) and diethyl(3-bromopropyl)-phosphonate (2.0 g, 7.7 mmol) was heated in a pressure tube at 130° C. for 4 hours. The mixture was allowed to cool to room temperature, and the resulting mass was dissolved in DMF (4 ml). The combined mixture was then added drop wise to ethyl acetate (40 ml). An oily residue was obtained which was washed with ethyl acetate (2×40 ml) and dried under vacuum to yield 1.9 g of Compound 23 which was then used without any further purification. The structure of Compound 23 is given below:

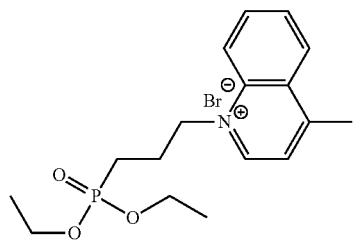 [SMILES: CCOP(=O)(CCC[n+]1ccc(C)c2ccccc21)OCC ; [Br-]]

(b) Preparation of Dye 115

A mixture of Compound 23 (0.53 g, 1.83 mmol), Compound 22 (0.67 g, 1.66 mmol) from step (c) of Example 18 and piperidine (72 µL, 0.73 mmol) was refluxed in ethanol (5 ml) for 18 hours. The reaction mixture was cooled to room temperature and ethanol was evaporated to yield 0.9 g (70%) of a dark blue solid (Dye 115). Abs (max, methanol)=570 nm; Em=640 nm, $\epsilon$=27,000 M$^{-1}$ cm$^{-1}$. The structure of Dye 115 is given below:

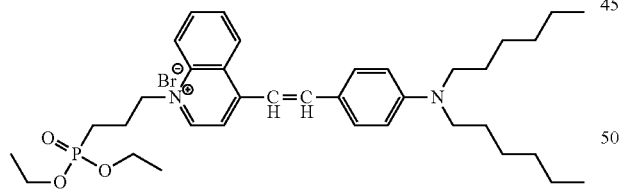

Example 21

Synthesis of Dye 116

This reaction was carried out as described previously in step (b) of Example 3, using a mixture of Compound 23 (0.67 g, 1.66 mmol) from step (a) of Example 20, 9-ethyl-3-carbazolecarboxaldehyde (0.41 g, 1.83 mmol), piperidine (72 µL, 0.73 mmol) and ethanol (5 ml). The resultant Dye 116 was precipitated using ethyl ether, as a brown solid (0.78 g, yield: 68%). Abs (max, methanol)=494 nm. The structure of Dye 116 is given below:

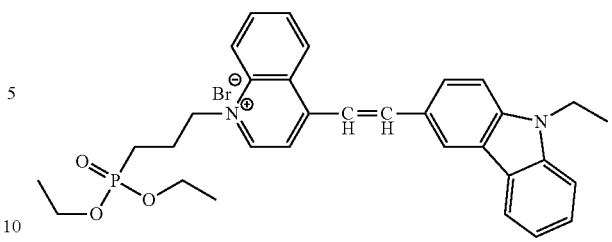

Example 22

Synthesis of Dye 117

This process was carried out as described previously for Example 5 except that in step (a), N,N'-diphenylformamidine (0.28 g, 1.4 mmol) was mixed with Compound 7 (0.5 g, 1.2 mmol) from Example 3 instead of Compound 4. This intermediate was then used as described previously in step (b) of Example 5 with 1-($\epsilon$-carboxypentynyl)-2,3,3-trimethylindoleninium-5-sulfonate (0.72 g, 2.0 mmol). The resultant Dye 117 was obtained as a purple solid (0.74 g). The structure of Dye 117 is given below:

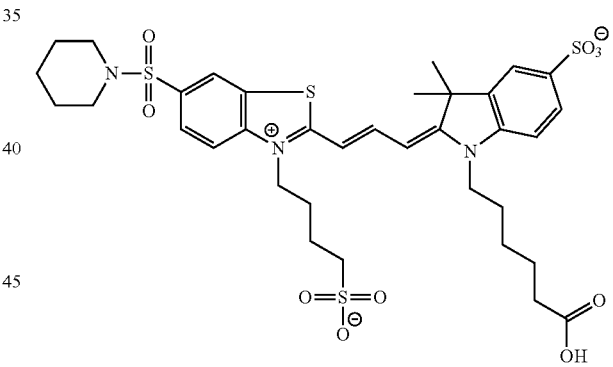

Example 23

Preparation of NHS Ester of Dye 117

This procedure was carried out as described previously in step (c) of Example 5, using Dye 117 (0.7 g, 0.88 mmol) from Example 22, N-hydroxysuccinimide (0.51 g, 4.4 mmol), DCC (1.0 g, 5.3 mmol) and DMF (9 ml). The NHS ester of Dye 117 was obtained as a purple solid (0.53 g). The structure of this compound is given below:

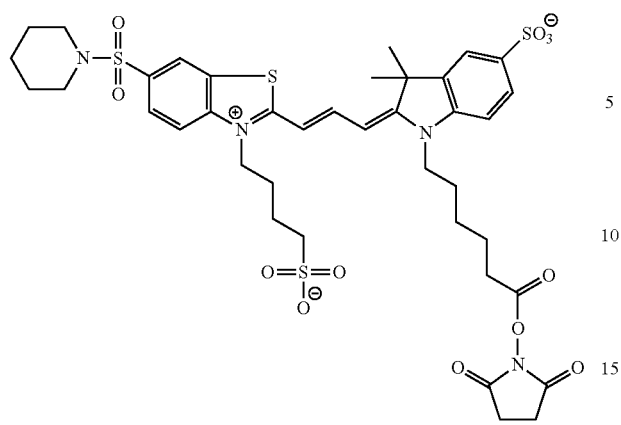

Example 24

Synthesis of Dye 118

A mixture of Compound 7 (1.0 g, 2.3 mmol) from step (a) of Example 3 and malonaldehyde bis(phenylimine) monohydrochloride (0.8 g, 3.0 mmol) in acetic acid (5 ml) and acetic anhydride was heated at 120° C. for 2 hours. The hot reaction mixture was then added to a solution of Compound 12 from step (a) of Example 11, dissolved in a mixture of pyridine (15 ml) and acetic anhydride (10 ml). The combined mixture was stirred at room temperature for 18 hrs and then centrifuged to remove some colored impurities. The supernatant was then added drop wise to a 10-fold excess of ethyl acetate. The precipitated dark colored solid was collected by centrifugation, washed with ethyl acetate and dried to yield 1.88 g of Dye 118. Abs (max, in 1×PBS pH 7.4)=651 nm; Em (max, in 1×PBS pH 7.4)=667 nm. The structure of Dye 118 is given below:

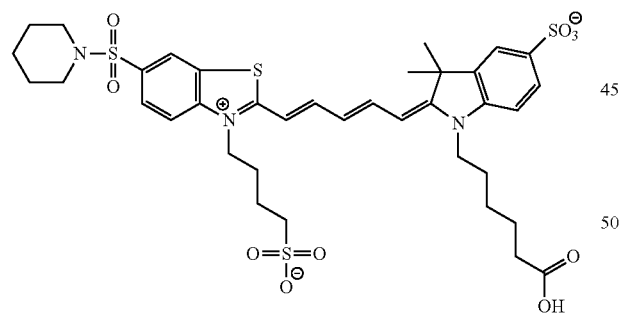

Example 25

Preparation of NHS Ester of Dye 118

This procedure was carried out as described previously in step (c) of Example 5, using Dye 118 (0.51 g, 0.62 mmol) from Example 24, N-hydroxysuccinimide (0.35 g, 3.0 mmol), DCC (0.62 g, 3.0 mmol) and DMF (10 ml). The NHS ester of Dye 117 was obtained as a dark blue solid (0.5 g). The structure of this compound is given below:

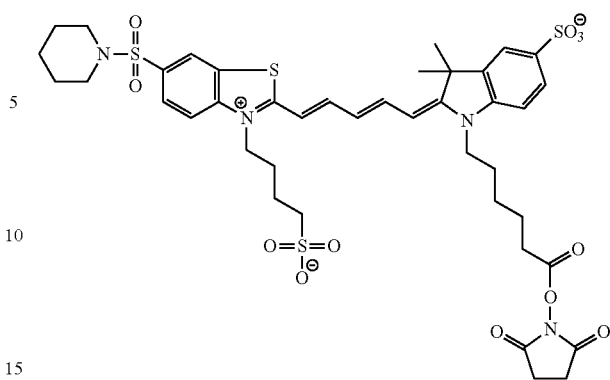

Example 26

Synthesis of Dye 119

A mixture of Compound 23 (0.67 g, 1.66 mmol) from step (a) of Example 20, 4-(dibutylamino)-benzaldehyde (0.43 g, 1.83 mmol) and piperidine (72 μL, 0.73 mmol) was refluxed in ethanol (5 ml) for 18 hours. The reaction mixture was cooled to room temperature and the ethanol was evaporated. The residue thus obtained was subjected to silica gel chromatography and the product eluted with 10% methanol in chloroform. Dye 119 was obtained as a dark blue gummy paste (0.65 g, 70%). Abs (max, methanol)=565 nm; Em=637 nm. The structure of Dye 119 is given below:

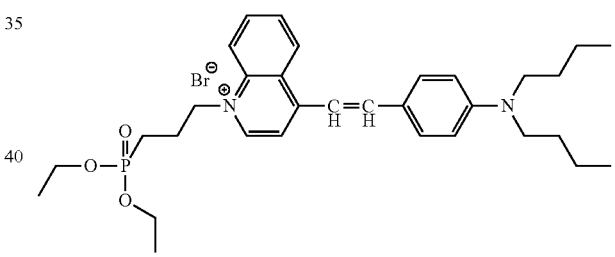

Example 27

Synthesis of Dye 120

(a) Preparation of N,N,2-trimethylbenzo[d]thiazole-6-sulfonamide (Compound 24)

A solution of Compound 2 (5.0 g, 20.2 mmol) from step (b) of Example 1 dissolved in tetrahydrofuran (THF, 30 ml) was added drop wise to a mixture of 2M N,N-dimethyl amine in THF (12 mL, 24.2 mmol) and triethylamine (5.6 ml, 40.4 mmol). The resultant mixture was stirred at room temperature for 3 hours. Solvents were removed by rotary evaporation and the residue thus obtained was partitioned between chloroform (100 ml) and water (100 ml). The organic layer was then washed with water (2×, 100 ml) and brine (1×, 100 ml), dried over sodium sulfate and evaporated. The oily residue thus obtained was dissolved in ca. 5 ml of hot ethyl acetate and this solution was then slowly added to 45 ml hexane. The mixture was cooled in the refrigerator overnight and the white solid that precipitated was collected, washed with hexane and dried to yield 4.8 g (93%) of Compound 24 whose structure is given below:

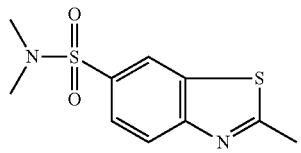

(b) Preparation of 6-(N,N-dimethylsulfamoyl)-2,3-dimethylbenzo[d]thiazole-3-ium tosylate (Compound 25)

A mixture of Compound 24 (2.0 g, 7.8 mmol) and p-toluenesulfonic acid methyl ester (2.2 g, 11.7 mmol) was heated in a pressure tube at 130° C. for 2 hours. The mixture was allowed to cool to room temperature, and the resulting mass was triturated with ethyl acetate (25 ml) until an off-white solid separated. The solid was collected by centrifugation, washed with ethyl acetate and dried under vacuum to yield 2.9 g (84%) of Compound 25 whose structure is given below:

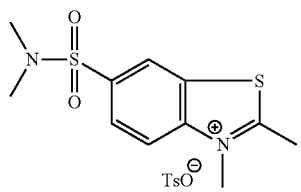

(c) Preparation of Dye 120

A mixture of Compound 25 (1.0 g, 2.3 mmol) and malonaldehyde bis (phenylimine) monohydrochloride (0.66 g, 2.53 mmol) in acetic acid (5 ml) and acetic anhydride was heated at 120° C. for 2 hours. The hot reaction mixture was then added to a solution of Compound 12 from step (a) of example 11 dissolved in pyridine (15 ml) and acetic anhydride (10 ml). The resultant mixture was stirred at room temperature for 18 hours and then centrifuged to remove some colored impurities. The supernatant was then added drop wise to a 10-fold excess of ethyl acetate. The dark colored precipitate was collected by centrifugation, washed with ethyl acetate and dried to yield 1.86 g of Dye 120. Abs (max, in 1×PBS pH 7.4)=652 nm. The structure of Dye 120 is given below:

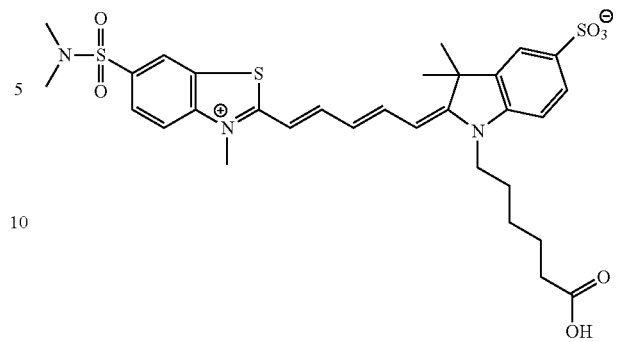

Example 28

Preparation of NHS Ester of Dye 120

This procedure was carried out as described previously in step (c) of Example 5, using Dye 120 (0.43 g, 0.64 mmol) from Example 27, N-hydroxysuccinimide (0.37 g, 3.2 mmol), DCC (0.66 g, 3.2 mmol) and DMF (10 ml). The NHS ester of Dye 120 was obtained as a dark blue solid (0.5 g). The structure of this dye is given below:

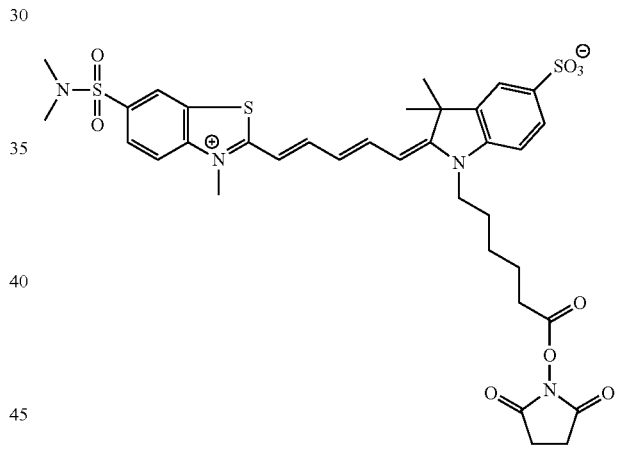

Example 29

Synthesis of Dye 121

(a) Preparation of 4-(6-(N,N-dimethylsulfamoyl)-2-methylbenzo[d]thiazole-3-ium-3-yl)butane-1-sulfonate (Compound 26)

A mixture of Compound 24 (2.55 g, 10.0 mmol) from step (a) of Example 27 and 1-4-butane sultone (2.98 g, 21.9 mmol) was heated in a pressure tube at 160° C. for 17 hours. The mixture was allowed to cool to room temperature, and the resulting mass was triturated with ethyl acetate (40 ml) until a pink solid separated. The solid was collected by centrifugation, washed with ethyl acetate and dried under vacuum to yield 3.58 g (92%) of Compound 26 with the structure:

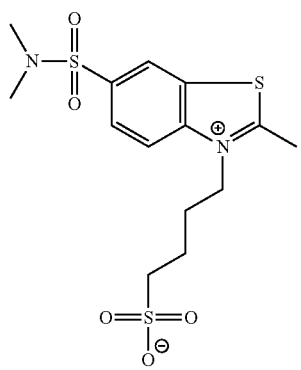

(b) Preparation of Compound 27

A mixture of Compound 12 (1.0 g, 2.12 mmol) from step (a) of Example 11 and N,N'-diphenylformamidine (0.46 g, 2.33 mmol) in acetic acid (5 ml) was heated and refluxed for 1.5 hours. The reaction mixture was cooled and added to a mixture of ethyl ether (20 ml) and ethyl acetate (20 ml). The precipitated orange solid was collected by centrifugation, washed with ethyl acetate (2×, 30 ml), dried under Argon and immediately used in the next step.

(c) Preparation of Dye 121

Compound 27 was added to a suspension of Compound 26 (1.4 g, 3.6 mmol) dissolved in acetic anhydride (10 ml) and pyridine (10 ml). The combined mixture was stirred in the dark at room temperature for 18 hours. The precipitated solid was collected by centrifugation, washed with a pyridine/acetic anhydride mixture (1:1, 30 ml), washed with ethyl acetate (2×, 30 ml) and dried to yield 0.71 g of a red solid (Dye 121). Abs (max, in water)=555 nm. The structure of Dye 121 is given below:

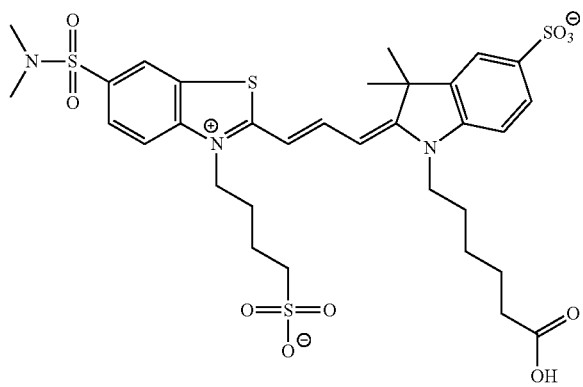

Example 30

Preparation of NHS Ester of Dye 121

This procedure was also carried out as described previously in step (c) of Example 5, using Dye 121 (0.25 g, 0.33 mmol) from Example 29, N-hydroxysuccinimide (0.19 g, 1.67 mmol), DCC (0.34 g, 1.67 mmol) and DMF (5 ml). The NHS ester of Dye 121 was obtained as a red solid (0.15 g). The structure of this dye is given below:

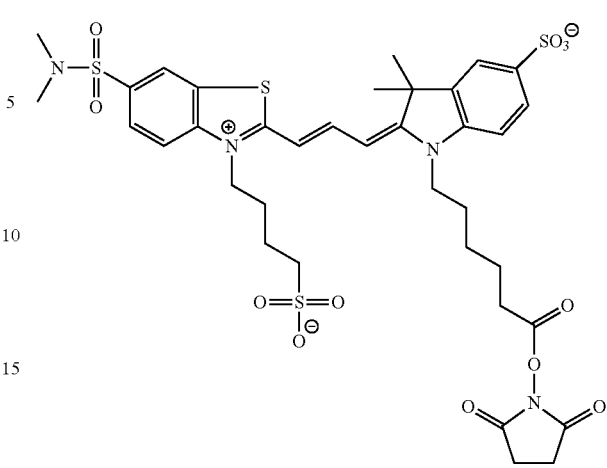

Example 31

Fluorescence Enhancement of Various Dyes Upon Binding to a Protein

Some of the dyes of the preceding examples were tested for changes in fluorescence upon binding to a protein (BSA). 1 μM of each dye was mixed with 150 μg of BSA in 10 mM TRIS (pH 7.5) with and without 0.05% SDS. Measurements were carried out on a standard fluorometer with and without BSA being present. Ratios were then calculated for the amount of fluorescence (emission maxima) in the presence of BSA compared to its absence. These results are given in Table 1.

TABLE 1

| Dye # | Fluorescence Enhancement with SDS | Fluorescence Enhancement without SDS |
|---|---|---|
| 101 | 140 | 33 |
| 103 | 10 | None |
| 113 | 33 | None |
| 114 | 70 | 6 |
| 115 | 78 | 100 |
| 116 | None | 12 |
| 119 | 92 | 95 |

Example 32

Preparation of Dye 122

Dye 109 from Example 14 was modified by dissolving in methanol and treated with an excess of concentrated HCl at room temperature for 5 minutes. After evaporation of solvents, the residue was washed with methylene chloride/ethyl acetate (1:1) two times to give Dye 122 whose structure is shown below:

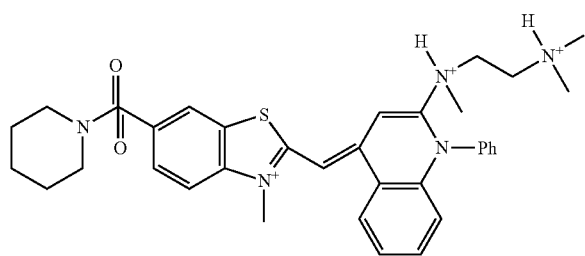

Example 33

Amplification of Nucleic Acids in the Presence of Dye 109

A target template was amplified on the Light Cycler (Roche) in the presence of various amounts of Dye 109 from Example 14. As a control, various amounts of SYBR Green (Molecular Probes, Eugene, Oreg.) were also included. The template was a 1:500 dilution of a 78 bp amplicon made in a previous reaction from the anti-sense C construct described in Liu et al. 1997 (J. Virol. 71: 4079-4085). A 2×PCR mix was made up of 20 mM Tris pH 8.3, 50 mM KCl, 4 mM $MgCl_2$, 0.4 mM dCTP, 0.4 mM dGTP, 0.4 mM dATP, 0.8 mM dUTP, 0.4 M Forward Primer and 0.4 mM Reverse Primer. The primers had the following sequences:

```
Forward Primer sequence = 5' CAT GAT CCG GAT GGG AGG TG 3'
Reverse Primer sequence = 5' GCA CAT CCG GAT AGT GAA TAG A 3'
```

A master mixture was made up of:
350 l of 2×PCR mix described above
14 l of 25 mM $MgCl_2$
122.5 l of DEPC treated $H_2O$
14 ul of 1 u/l ung (Epicentre)
7 l of 10 mg/ml BSA (New England Biolabs, Beverly, Mass.)
7 l Taq polymerase (Perkin Elmer)+7 l of TaqStart (Clontech)
2.5 l of target template+2.0 l of various dilutions of dyes were added to 15.5 l of Master mixture, incubated at 45° C. for 10 minutes and then amplified by:
1) Melting
   2 minutes @ 95° C.
2) Cycling
   a) Denaturation step: 0 seconds @ 95° C.
   b) Annealing step: 5 seconds @ 69° C. for first cycle; subsequent cycles were each reduced by 0.5° C. until 65° C. was reached and all annealing steps in further cycles were carried out at this temperature
   c) Extension step: 5 seconds @ 72° C.
3) After completion of 56 cycles, all samples were maintained at 4° C. until analyzed.

The samples were analyzed for detection of real time synthesis in the Light Cycler and it was seen that dye 109 could be used for this purpose (data not shown). After the amplification reactions were finished, the samples were analyzed by gel electrophoresis. The gel analysis of these reaction products is shown in FIG. 1. For SYBR Green, the recommended reaction concentration is 1:10,000. As such, the amplification products shown in lanes 5 and 6 using 2 l of 1:800 dilution in a 20 l reaction (final=1:8,000) is approximately representative of the product from the standard procedure. For Dye 109, the reactions are listed in terms of dilutions of a stock of Dye 109 with an OD reading of 200 taken at 495 nm. As seen in FIG. 1, for both the 1:20 dilution of SYBR Green and undiluted Dye 109 stock, a strong inhibition of amplification was seen with little or no product being synthesized. However, when lower dilutions of the dyes were added there was no inhibition of the process. Furthermore, this Example demonstrates that at lower concentrations (1:200 dilution of SYBR Green in lane 7 and 1:25 dilution of Dye 109 in lanes 11 and 12), two unexpected but beneficial results were observed: a) enhancement of overall synthesis of target derived amplicons compared to the reaction without any dye and b) elimination or suppression of the synthesis of non-target derived amplicons seen in the absence of dye and at most of the tested dye concentrations.

Example 34

Amplification of Nucleic Acids in the Presence of Dye 109 Using a Standard PCR Machine The experiment shown in Example 33 was repeated using a standard PCR machine for synthesis to see if the effects observed in Example 33 was dependent upon the rapid heating and cooling steps used in the Light Cycler.

A master mixture was made up of:
500 l of 2×PCR mix described in example 33
20 l of 25 mM $MgCl_2$
175 l of DEPC treated $H_2O$
10 ul of 1 u/l ung (Epicentre)
10 l of 10 mg/ml BSA (New England Biolabs, Beverly, Mass.)
10 l Taq polymerase (Perkin Elmer)+10 l of TaqStart (Clontech)

PCR conditions were 2.5 l of target template+2.0 l of dye was added to 15.5 l of Master mixture incubated at 45° C. for 10 minutes and then amplified using cycles of:
a) 94° C. for 30 seconds
b) 65° C. for 30 seconds
c) 72° C. for 1 minute A duplicate set of samples was amplified with one set being taken out after 20 cycles of amplification and the second set undergoing 40 cycles. The gel analysis for this set of amplification reactions is shown in FIG. 2. It can be seen that after 20 cycles, a single discrete band can be seen for the 1:200 dilution of SYBR Green (Lanes 5 and 6) whereas all other SYBR Green dilutions and in the absence of any dye, no synthesis was evident. Similarly for Dye 109, a single discrete band can be seen for the 1:10 dilution (lanes 12 and 13), lesser amounts of synthesis with the 1:15 dye dilution samples (lanes 14 and 15) and faint bands at slightly lower dye concentrations (1:20 and 1:25 in lanes 16/17 and 18/19 respectively). This indicates that under these conditions there was more efficient synthesis of amplicons in the presence of SYBR Green and Dye 109 at these concentrations, qualitatively repeating the results of Example 33. After 40 cycles, synthesis was observed at all concentrations except the high dye samples in lanes 7, 9, 10 and 11. The other effect previously observed was also seen, i.e. non-target amplicon synthesis seen in the no Dye reaction (lane 1) was reduced with the 1:200 dilution of SYBR Green and the 1:10 dilution of Dye 109 again repeating the results of Example 33.

Example 35

Amplification of Nucleic Acids in the Presence of Dye 122 and 109a

A target template was amplified on the Light Cycler (Roche) in the presence of various amounts of SYBR Green and Dye 122 from Example 32. In addition, a byproduct from the silica gel chromatography of Dye 109 in step (g) of Example 14 was also used. This compound is believed to have a single protonation of one of the amines of Dye 109 and as such will be termed Dye 109a. The stock of Dye 122 was OD=200 measured at 488 nm and the stock of Dye 109a was OD=200 measured at 498 nm. The template was a 1:50,000 dilution of the 78 bp amplicon of the anti-sense C construct described previously.
A master mixture was made up of:
350 l of 2×PCR mix described in Example 33
14 l of 25 mM MgCl$_2$
175.0 l of DEPC treated H$_2$O
7 l of 10 mg/ml BSA (New England Biolabs, Beverly, Mass.)
7 l Taq polymerase (Perkin Elmer)+7 l of TaqStart (Clontech)
2.0 l of target template+2.0 l of various dye dilutions were added to 16 l of Master mixture, and then amplified as described previously in Example 33 except that the incubation at 45° C. for 10 minutes was eliminated since ung was not used for this series of amplifications. The amplification was stopped after 19 cycles. The results of this series of amplifications are seen in FIG. 3. For SYBR Green, the 1:800 dilution (lanes 4 and 5) gave the best amplification with a sharp drop off on either side. For Dye 122, the 1:10 dilution (lane 10) was inhibitory while the 1:30 dilution (lanes 11 and 12) was the best with less amplification seen for the next dye dilutions (1:100 etc.). For Dye 109a, similar features were seen where 1:10 was inhibitory (lane 18) and 1:30 was optimal (lanes 19 and 20).

Example 36

Amplification of Nucleic Acids in the Presence of Dye 122 and 109a

Although the previous example showed a significant improvement of amplification for Dye 109a and 122, there was a fairly substantial difference between the best concentration of dye and the next higher and lower dilutions of dyes. A series of dilutions that were closer together was carried out for both Dye 109a and Dye 122. The target template was amplified on the Light Cycler and the template was the 1:50,000 dilution of the 78 bp amplicon of the anti-sense C construct described previously.
A master mixture was made up as described previously in Example 35.
2.0 l of target template (1:50,000 dilution of the antisense C amplicon)+2.0 l of various dye concentrations were added to 16 l of Master mix and then amplified as described previously in Example 33 and stopping after 17 amplification cycles. Samples taken from these amplification reactions are shown in FIG. 4. As seen in these results, a fairly broad spectrum of dilutions can give a strong enhancement effect for both Dye 122 and Dye 109a.

Example 37

Amplification of Various Amounts of Nucleic Acids in the Presence of Dye 122 and 109a In the previous experiments, a fixed amount of target was amplified in the presence of varying level of dyes. The eventual use of these dyes is going to be with a fixed amount of dye and varying levels of targets. As such, an experiment was carried out using previously determined optimal levels of dyes and various amounts of input target (again using the anti-sense C as a model).

Dilution 1=1:100,000

Dilution 2=1:1,000,000

Dilution 3=1:10,000,000

Dilution 4=1:100,000,000

Dilution 5=1:1,000,000,000

Dilution 6=1:10,000,000,000

Selected amounts of target template were amplified on the Light Cycler (Roche) in the presence of various amounts of Dye 122, Dye 109a and SYBR Green.

A master mixture was made up of:
380 l of 2×PCR mix described in Example 33
15.2 l of 25 mM MgCl$_2$
190.0 l of DEPC treated H$_2$O
7.6 l of 10 mg/ml BSA (New England Biolabs, Beverly, Mass.)
7.6 l Taq polymerase (Perkin Elmer)+7.6 l of TaqStart (Clontech)
2.0 l of target template (1:50,000 dilution of the antisense C amplicon)+2.0 l of various dye concentrations were added to 16 l of Master mixture and amplified as described previously in Example 33 stopping after 29 cycles. Dye additions were from the 1:1000 dilution of SYBR Green, 1:30 of Dye 109a and 1:30 of Dye 122. Samples taken from these amplification reactions are shown in FIG. 5.

At the highest input level (Dil 2 1:1,000,000 dilution of amplicon) no evidence of amplification is seen in the sample without dye. On the other hand, a faint but visible band can be seen for the sample that included SYBR Green. Further dilutions of target do not show any evidence of an amplification product for the SYBR Green samples. More interestedly, it can be seen that for the samples that included Dyes 109a and 122, a strong prominent band can be seen with the Dil 2 (1:1,000,000) input level and visible bands for the inputs that had been diluted 10-100× more.

Many obvious variations will be suggested to those of ordinary skill in the art in light of the above detailed descriptions of the present invention. All such obvious variations are fully contemplated and are embraced by the scope and spirit of the present invention as set forth in the claims that now follow.

What is claimed is:
1. A dye having the structure:

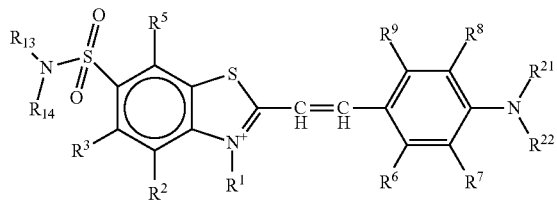

wherein
at least one of $R^8$ and $R^{21}$ or $R^7$ and $R^{22}$ are taken together to form a five-membered or six-membered saturated or unsaturated heteroalkyl ring;
at least one of $R^1$, $R^2$, $R^3$, $R^6$, $R^7$, $R^8 R^9$, $R^{21}$ or $R^{22}$ is Q, wherein Q is selected from a sulfoxide ($SOR^{13}$), a sulfone ($SO_2CR^{13}R^{14}R^{15}$), a sulfonamide ($SO_2NR^{13}R^{14}$), a phosphonate ($PO_3^=$), a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), a thioanalogue of a phosphonamide, ($PSNR^{13}R^{14}NR^{19}R^{20}$), a phosphoramide ($PONR^{13}R^{14}NR^{15}NR^{19}R^{20}$), a thioanalogue of a phosphoramide ($PSNR^{13}R^{14}NR^{15}NR^{19}R^{20}$), a phosphoramidite ($PO_2R^{19}NR^{13}R^{14}$), a thioanalogue of a phosphoramidite ($POSR^{19}R^{13}R^{14}$), wherein E is O or S;
wherein Q is attached directly, or indirectly through a saturated or unsaturated, linear or branched, substituted or unsubstituted carbon linker arm, which may further comprise one or more heteroatoms selected from sulfur, oxygen and nitrogen, and wherein when Q is a sulfonamide, it does not comprise a terminal reactive group or a linker joining the dye to a target molecule;
$R^{13}$, $R^{14}$, $R^{15}$, $R^{19}$ and $R^{20}$ are independently selected from hydrogen, halogen, an amino group, a saturated or unsaturated, linear or branched, substituted or unsubstituted alkyl group, or when taken together $R^{13}$ and $R^{14}$ form a five-membered or six-membered saturated or unsaturated heteroalkyl ring;
wherein the remaining $R^1$, $R^2$, $R^3$, $R^5$, $R^6$, $R^7$, $R^8$, $R^9$, $R^{21}$ and $R^{22}$ are independently selected from hydrogen, Z, a saturated or unsaturated, linear or branched, substituted or unsubstituted alkyl group, a saturated or unsaturated, linear or branched, substituted or unsubstituted alkyl group alkoxy group, or when taken together, $R^2$ and $R^3$, $R^6$ and $R^7$, and $R^8$ and $R^9$ form a five-membered or six-membered ring;

Z is selected from a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^\equiv$), a phosphate monoester ($PO_2^-ER^{13}$), a phosphate diester ($PO_2ER^{13}ER^{14}$), a phosphonate ($PO_3^\equiv$) a phosphonate monoester ($PSO_2^-ER^{13}$) a phosphonate diester ($POER^{13}ER^{14}$), a thiophosphate ($PSO_3^\equiv$), a thiophosphate monoester ($PSO_2^-ER^{13}$) a thiophosphate diester ($PSOER^{13}ER^{14}$), a thiophosphonate ($PSO_2^\equiv$), a thiophosphonate monoester ($PSO^-ER^{13}$) a thiophosphonate diester ($PSER^{13}ER^{14}$), a phosphonamide ($PONR^{13}R^{14}NR^{19}R^{20}$), a thioanalogue of a phosphonamide ($PSNR^{13}R^{14}NR^{19}R^{20}$), a phosphoramide ($PONR^{13}R^{14}NR^{15}NR^{19}R^{20}$), a thioanalogue of a phosphoramide ($PSNR^{13}R^{14}NR^{15}NR^{19}R^{20}$), a phosphoramidite ($PO_2R^{19}NR^{13}R^{14}$) or a thioanalogue of a phosphoramidite ($POSR^{19}NR^{13}R^{14}$), and E is O or S;

wherein Z is attached directly or indirectly through a saturated or unsaturated, linear or branched, substituted or unsubstituted carbon linker arm, which may further comprise one or more heteroatoms selected from sulfur, oxygen and nitrogen;

and wherein any of $R^1$, $R^2$, $R^3$, $R^5$, $R^6$, $R^7$, $R^8$, $R^9$, $R^{21}$ or $R^{22}$ may further comprise a heteroatom containing side chain wherein said side chain is joined to the R group by a linkage selected from an ether linkage ($-OR^{25}$), a thioether linkage ($-SR^{25}$), and an amine linkage ($-NR^{25}R^{26}$ or $-N^+R^{25}R^{26}R^{27}$), and wherein $R^{25}$, $R^{26}$ and $R^{27}$ are each independently selected from hydrogen, Z, a saturated or unsaturated, linear or branched, substituted or unsubstituted alkyl group, a saturated or unsaturated, linear or branched, substituted or unsubstituted alkoxy group, or when taken together, $R^{25}$ and $R^{26}$, or $R^{26}$ and $R^{27}$ form a saturated or unsaturated five-membered or six-membered alkyl or heteroalkyl ring, and wherein any of $R^{25}$, $R^{26}$ or $R^{27}$ may further comprise a heteroatom containing side chain.

2. The compound of claim 1 wherein at least one of $R^1$, $R^2$, $R^3$, $R^5$, $R^6$, $R^7$, $R^8$, $R^9$, $R^{21}$ or $R^{22}$ comprises a reactive group, said reactive group comprising a nucleophilic reactive group, an electrophilic reactive group, a terminal alkene, a terminal alkyne, a coordinate group or an alkylating agent.

3. The dye of claim 1, having the structure:

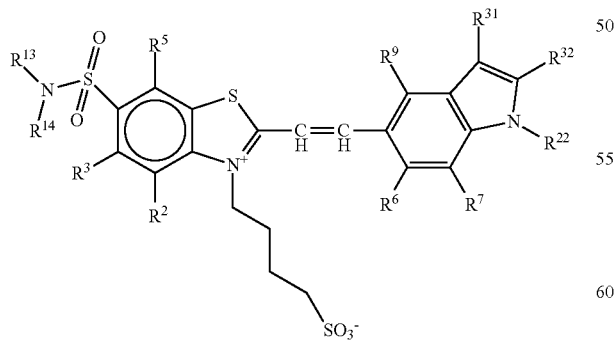

wherein $R^{31}$ and $R^{32}$ are each independently selected from hydrogen, Z, a saturated or unsaturated, linear or branched, substituted or unsubstituted alkyl group, a saturated or unsaturated, linear or branched, substituted or unsubstituted alkoxy group, or when taken together, $R^7$ and $R^{22}$, $R^{22}$ and $R^{32}$, $R^{32}$ and $R^{31}$, or $R^{31}$ and $R^9$ form a five-membered or six-membered saturated or unsaturated alkyl or heteroalkyl ring, wherein any of $R^{31}$ and $R^{32}$ may further comprise a heteroatom containing side chain wherein said side chain is joined to the R group by a linkage selected from an ether linkage ($-OR^{25}$), a thioether linkage ($-SR^{25}$), and an amine linkage ($-NR^{25}R^{26}$ or $-N^+R^{25}R^{26}R^{27}$), and wherein $R^{25}$, $R^{26}$ and $R^{27}$ are each independently selected from hydrogen, Z, a saturated or unsaturated, linear or branched, substituted or unsubstituted alkyl group, a saturated or unsaturated, linear or branched, substituted or unsubstituted alkoxy group, or when taken together, $R^{25}$ and $R^{26}$, or $R^{26}$ and $R^{27}$ form a saturated or unsaturated five-membered or six-membered alkyl or heteroalkyl ring, and wherein any of $R^{25}$, $R^{26}$ or $R^{27}$ may further comprise a heteroatom containing side chain.

4. The dye of claim 3, having the structure:

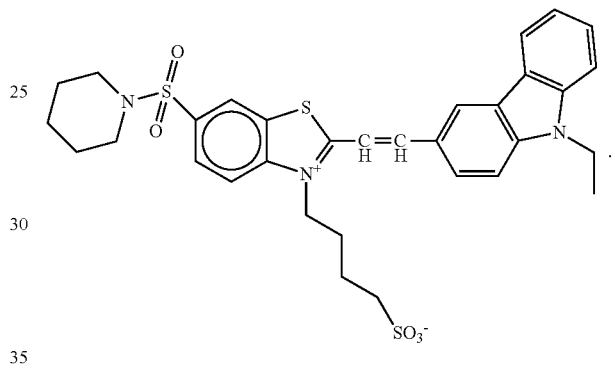

5. The dye of claim 1 having the structure:

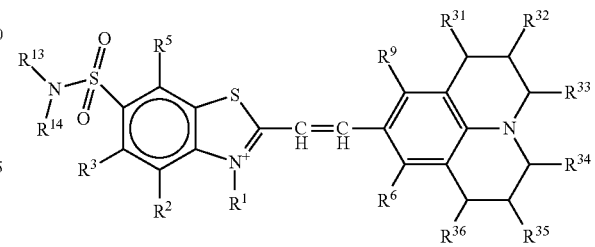

wherein $R^{31}$, $R^{32}$, $R^{33}$, R $R^{34}$, $R^{35}$ and $R^{36}$ are independently selected from hydrogen, Q, Z, a saturated or unsaturated, linear or branched, substituted or unsubstituted alkyl group, and a saturated or unsaturated, linear or branched, substituted or unsubstituted alkoxy group, any of $R^{31}$, $R^{32}$, $R^{33}$, $R^{34}$, $R^{35}$ and $R^{36}$ may further comprise a heteroatom containing side chain wherein said side chain is joined to the R group by a linkage selected from an ether linkage ($-OR^{25}$), a thioether linkage ($-SR^{25}$), and an amine linkage ($-NR^{25}R^{26}$ or $-N^+R^{25}R^{26}R^{27}$), and wherein $R^{25}$, $R^{26}$ and $R^{27}$ are independently selected from hydrogen, Z, a saturated or unsaturated, linear or branched, substituted or unsubstituted alkyl group, and a saturated or unsaturated, linear or branched, substituted or unsubstituted alkoxy group, or when taken together, $R^{25}$ and $R^{26}$, or $R^{26}$ and $R^{27}$ form a saturated or unsaturated five-membered or six-membered alkyl or heteroalkyl ring, and wherein any of $R^{25}$, $R^{26}$ or $R^{27}$ may further comprise a heteroatom containing side chain.

6. The dye of claim 5, having the structure:

[Chemical structure]

7. The dye of claim 5, having the structure:

[Chemical structure]

8. The dye of claim 1, having the structure:

[Chemical structure]

9. The dye of claim 2, wherein said nucleophilic reactive group is a thiol, amine or hydroxyl group.

10. The dye of claim 2, wherein said electrophilic reactive group is an isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal or aldehyde group.

11. The dye of claim 2, wherein said alkyl or alkoxy groups independently comprise from 1-18 carbons.

12. The dye of claim 11, wherein said alkyl or alkoxy groups independently comprise from 1-6 carbons.

13. The dye of claim 11, wherein said dye further comprises one or more charged groups or polar groups.

14. The dye of claim 13, wherein at least one of said one or more charged groups or polar groups is monomeric.

15. The dye of claim 13, wherein at least one of said one or more charged groups or polar groups is polymeric.

16. The dye of claim 13, wherein at least one of said one or more charged groups or polar groups is anionic.

17. The dye of claim 13, wherein at least one of said one or more charged groups or polar groups is cationic.

18. The dye of claim 2, wherein said dye further comprises one or more anionic charged groups or polar groups and one or more cationic charged groups or polar groups.

19. The dye of claim 2, wherein said dye is linked to a target molecule through said reactive group.

20. The dye of claim 19, wherein said target molecule comprises a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, glycolipid, viral particle, viral component, bacterial cell, bacterial component, eucaryotic cell, eukaryotic cell component, natural drug, synthetic drug, glass particle, glass surface, plastic particle, plastic surface, silicaceous particle, silicaceous surface, organic molecule, dye or a derivative thereof.

21. The dye of claim 20, wherein said nucleoside, nucleotide, oligonucleotide, or polynucleotide comprises one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues or any combination thereof.

22. The dye of claim 19, wherein said dye is linked to said target molecule through a linker arm.

23. The dye of claim 22, wherein said linker arm is attached to said target molecule through a bond which comprises a covalent bond, a non-covalent bond, a polar bond or a coordinate bond.

24. The oligonucleotide or polynucleotide of claim 20, wherein said oligonucleotide or polynucleotide comprises two or more dye molecules attached to separate nucleotides of said oligonucleotide or polynucleotide.

25. The oligonucleotide or polynucleotide of claim 24, wherein said two or more dye molecules comprise the same dye molecules.

26. The oligonucleotide or polynucleotide of claim 24, wherein said two or more dye molecules comprise different dye molecules.

27. A composite dye comprising the dye of claim 20, wherein said target molecule comprises a dye.

28. The composite dye of claim 27 further comprising a nucleophilic reactive group, an electrophilic reactive group, a terminal alkene, a terminal alkyne, a coordinate group or an alkylating agent.

29. The dye of claim 2, wherein said dye has been linked to a target specific moiety through said reactive group.

30. The dye of claim 29, wherein said target specific moiety comprises a protein or a nucleic acid.

31. The dye of claim 30, wherein said protein comprises an antibody or a fragment thereof.

32. The dye of claim 30, wherein said nucleic acid comprises unmodified nucleotides, modified nucleotides, nucleotide analogues or any combination thereof.

* * * * *